United States Patent
Myers et al.

(10) Patent No.: US 11,511,054 B2
(45) Date of Patent: Nov. 29, 2022

(54) USE OF ANTISTATIC MATERIALS IN THE AIRWAY FOR THERMAL AEROSOL CONDENSATION PROCESS

(71) Applicant: Alexza Pharmaceuticals, Inc., Mountain View, CA (US)

(72) Inventors: Daniel J. Myers, Mountain View, CA (US); Khe Kubel, San Mateo, CA (US); James Cassella, Essex, CT (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 685 days.

(21) Appl. No.: 15/557,030

(22) PCT Filed: Mar. 9, 2016

(86) PCT No.: PCT/US2016/021554
§ 371 (c)(1),
(2) Date: Sep. 11, 2017

(87) PCT Pub. No.: WO2016/145075
PCT Pub. Date: Sep. 15, 2016

(65) Prior Publication Data
US 2019/0117909 A1    Apr. 25, 2019

Related U.S. Application Data

(60) Provisional application No. 62/131,823, filed on Mar. 11, 2015.

(51) Int. Cl.
*A61M 11/04*    (2006.01)
*A61K 9/12*    (2006.01)
(Continued)

(52) U.S. Cl.
CPC ........... *A61M 11/042* (2014.02); *A61K 9/007* (2013.01); *A61K 9/0073* (2013.01); *A61K 9/12* (2013.01);
(Continued)

(58) Field of Classification Search
CPC .......................... A61M 11/042; A61M 15/02; A61M 15/0086; A61M 2202/025;
(Continued)

(56) References Cited

U.S. PATENT DOCUMENTS 3,150,020 A    9/1964  Kilmer
3,695,179 A    10/1972 Rainone
(Continued)

FOREIGN PATENT DOCUMENTS

CN    1120109 A    4/1996
CN    1514719 A    7/2004
(Continued)

OTHER PUBLICATIONS

Terry L. Welsher, Timothy J. Blondin, G. Theodore Dangelmayer, and Yehuda Smooha. "Design for Electrostatic-Discharge (ESD) Protection in Telecommuncations Products". AT&TTechnicalJournal. May/Jun. 1990. (Year: 1990).*

(Continued)

*Primary Examiner* — Valerie L Woodward
*Assistant Examiner* — Paige Kathleen Bugg
(74) *Attorney, Agent, or Firm* — Adsero IP

(57) ABSTRACT

The disclosure teaches the use of antistatic materials in the airway for thermal aerosol generation devices. The present disclosure teaches the use of antistatic materials for drug delivery in any drug that may be susceptible to charging during aerosol generation.

16 Claims, 3 Drawing Sheets

(51) Int. Cl.
  *A61M 15/00* (2006.01)
  *A61K 31/5517* (2006.01)
  *A61K 9/00* (2006.01)
  *A61M 15/02* (2006.01)

(52) U.S. Cl.
  CPC ..... *A61K 31/5517* (2013.01); *A61M 15/0086* (2013.01); *A61M 15/02* (2013.01); *A61M 2202/025* (2013.01); *A61M 2202/0266* (2013.01); *A61M 2205/0233* (2013.01); *A61M 2205/8206* (2013.01)

(58) Field of Classification Search
  CPC .. A61M 2202/0266; A61M 2205/0233; A61M 2205/8206; A61K 9/007; A61K 9/0073; A61K 9/12; A61K 31/5517
  USPC .................................................. 128/200.14
  See application file for complete search history.

(56) References Cited

U.S. PATENT DOCUMENTS

| | | |
|---|---|---|
| 3,791,302 A | 2/1974 | McLeod |
| 3,792,302 A | 2/1974 | Downing |
| 3,831,606 A | 8/1974 | Damani |
| 3,882,323 A | 5/1975 | Smolker |
| 3,971,377 A | 7/1976 | Damani |
| 3,982,095 A | 9/1976 | Robinson |
| 4,013,061 A | 3/1977 | Trumble |
| 4,020,379 A | 4/1977 | Manning |
| 4,045,156 A | 8/1977 | Chu |
| 4,047,483 A | 9/1977 | Wlilliams |
| 4,059,388 A | 11/1977 | Shaffer |
| 4,189,200 A | 2/1980 | Yeager |
| 4,193,388 A | 3/1980 | Frosch |
| 4,236,544 A | 12/1980 | Osaka |
| 4,354,432 A | 10/1982 | Cannavo |
| 4,369,269 A | 1/1983 | Harper |
| 4,372,213 A | 2/1983 | Rozner |
| 4,374,686 A | 2/1983 | Davitt |
| 4,419,650 A | 12/1983 | John |
| 4,443,495 A | 4/1984 | Morgan |
| 4,484,577 A | 11/1984 | Sackner |
| 4,508,755 A | 4/1985 | Reintjes |
| 4,627,963 A | 12/1986 | Olson |
| 4,700,629 A | 10/1987 | Benson |
| 4,708,151 A | 11/1987 | Shelar |
| 4,714,082 A | 12/1987 | Banerjee |
| 4,756,318 A | 7/1988 | Clearman |
| 4,793,366 A | 12/1988 | Hill |
| 4,819,665 A | 4/1989 | Roberts |
| 4,854,331 A | 8/1989 | Banerjee |
| 4,881,556 A | 11/1989 | Clearman |
| 4,892,037 A | 1/1990 | Betts |
| 4,922,901 A | 5/1990 | Brooks |
| 4,935,073 A | 6/1990 | Bartlett |
| 4,947,874 A | 8/1990 | Brooks |
| 4,947,875 A | 8/1990 | Brooks |
| 4,952,903 A | 8/1990 | Shibata |
| 4,989,619 A | 2/1991 | Clearman |
| 5,020,548 A | 6/1991 | Farrier |
| 5,027,707 A | 7/1991 | Mei |
| 5,033,483 A | 7/1991 | Clearman |
| 5,042,509 A | 8/1991 | Banerjee |
| 5,060,666 A | 10/1991 | Clearman |
| 5,060,671 A | 10/1991 | Counts |
| 5,067,499 A | 11/1991 | Banerjee |
| 5,095,921 A | 3/1992 | Loose |
| 5,105,831 A | 4/1992 | Banerjee |
| 5,135,009 A | 8/1992 | Muller |
| 5,144,962 A | 9/1992 | Counts |
| 5,179,966 A | 1/1993 | Losee |
| 5,224,498 A | 7/1993 | Deevi |
| 5,249,586 A | 10/1993 | Morgan |
| 5,269,327 A | 12/1993 | Counts |
| 5,285,798 A | 2/1994 | Banerjee |
| 5,322,018 A | 6/1994 | Hadden |
| 5,322,075 A | 6/1994 | Deevi |
| 5,345,951 A | 9/1994 | Serrano |
| 5,357,984 A | 10/1994 | Farrier |
| 5,407,473 A | 4/1995 | Miura |
| 5,408,574 A | 4/1995 | Deevi |
| 5,415,161 A | 5/1995 | Ryder |
| 5,468,936 A | 11/1995 | Deevi |
| 5,479,948 A | 1/1996 | Counts |
| 5,505,214 A | 4/1996 | Collins |
| 5,509,354 A | 4/1996 | Dorffler |
| 5,554,646 A | 5/1996 | Lloyd |
| 5,538,020 A | 7/1996 | Farrier |
| 5,549,849 A | 8/1996 | Namura |
| 5,564,442 A | 10/1996 | MacDonald |
| 5,573,565 A | 11/1996 | Dalton |
| 5,584,701 A | 12/1996 | Lampotang |
| 5,591,368 A | 1/1997 | Fleischhauer |
| 5,593,792 A | 1/1997 | Farrier |
| 5,603,350 A | 2/1997 | Stoll |
| 5,613,504 A | 3/1997 | Collins |
| 5,613,505 A | 3/1997 | Campbell |
| 5,623,115 A | 4/1997 | Lauritzen |
| 5,626,360 A | 5/1997 | Lauritzen |
| 5,649,554 A | 7/1997 | Sprinkel |
| 5,672,843 A | 9/1997 | Evans |
| 5,686,691 A | 11/1997 | Hamilton |
| 5,694,919 A | 12/1997 | Rubsamen |
| 5,705,261 A | 1/1998 | Axelson |
| 5,735,263 A | 4/1998 | Rubsamen |
| 5,845,578 A | 12/1998 | Fogle, Jr. |
| 5,845,933 A | 12/1998 | Walker |
| 5,853,810 A | 12/1998 | Zhang et al. |
| 5,865,185 A | 2/1999 | Collins |
| 5,878,752 A | 3/1999 | Adams |
| 5,890,908 A | 4/1999 | Lampotang |
| 5,906,281 A * | 5/1999 | Fujikawa ............. H05K 9/0067 206/719 |
| 5,915,378 A | 6/1999 | Lloyd |
| 5,934,272 A | 8/1999 | Lloyd |
| 5,957,124 A | 9/1999 | Lloyd |
| 5,960,792 A | 10/1999 | Lloyd |
| 6,014,970 A | 1/2000 | Ivri |
| 6,053,176 A | 4/2000 | Adams |
| 6,062,210 A | 5/2000 | Welles |
| 6,090,403 A | 7/2000 | Block |
| 6,095,153 A | 8/2000 | Kessler |
| 6,102,036 A | 8/2000 | Slutsky |
| 6,164,287 A | 12/2000 | White |
| 6,190,326 B1 | 2/2001 | McKinnon |
| 6,289,813 B1 | 9/2001 | Duguet |
| 6,325,475 B1 | 12/2001 | Hayes |
| 6,328,033 B1 | 12/2001 | Avrahami |
| 6,390,453 B1 | 5/2002 | Frederickson |
| 6,478,903 B1 | 11/2002 | John |
| 6,632,380 B1 | 10/2003 | Wessling |
| 6,648,950 B2 | 11/2003 | Lee |
| 6,660,632 B2 | 12/2003 | Hill |
| 6,671,945 B2 | 1/2004 | Gerber |
| 6,680,668 B2 | 1/2004 | Gerber |
| 6,682,716 B2 | 1/2004 | Hodges et al. |
| 6,684,880 B2 | 2/2004 | Trueba |
| 6,713,399 B1 | 3/2004 | Kao |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,776,978 B2 | 8/2004 | Rabinowitz et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |

(56) References Cited

U.S. PATENT DOCUMENTS

| | | |
|---|---|---|
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,812,432 B1 | 11/2004 | Haluschka |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 * | 3/2006 | Rabinowitz .............. A61P 25/20 128/200.14 |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Hale et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,494,344 B2 | 2/2009 | Galauner et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,785,482 B2 | 8/2010 | Subramanian |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz |
| 8,235,037 B2 | 8/2012 | Hale |
| 8,288,372 B2 | 10/2012 | Hale |
| 8,333,197 B2 | 12/2012 | Cross et al. |
| 8,387,612 B2 | 3/2013 | Damani et al. |
| 8,425,704 B2 | 4/2013 | Currano |
| 8,506,935 B2 | 8/2013 | Hale et al. |
| 8,955,512 B2 | 2/2015 | Hales et al. |
| 8,991,387 B2 | 3/2015 | Damani et al. |
| 9,211,382 B2 | 12/2015 | Hale et al. |
| 9,308,208 B2 | 4/2016 | Wensley |
| 9,370,629 B2 | 6/2016 | Damani |
| 9,439,907 B2 | 9/2016 | Hale et al. |
| 9,440,034 B2 | 9/2016 | Hale et al. |
| 9,687,487 B2 | 6/2017 | Hodges et al. |
| 9,724,341 B2 | 8/2017 | Myers et al. |
| 10,166,224 B2 | 1/2019 | Myers et al. |
| 10,350,157 B2 | 7/2019 | Hale |
| 10,625,033 B2 | 4/2020 | Wensley |
| 10,786,635 B2 | 9/2020 | Sharma |
| 2002/0000225 A1 | 1/2002 | Schuler |
| 2002/0035945 A1 | 3/2002 | Knowlton |
| 2002/0036192 A1 | 3/2002 | Sato |
| 2002/0037437 A1 | 3/2002 | Yamamoto |
| 2002/0097139 A1 | 7/2002 | Gerber |
| 2002/0185485 A1 | 12/2002 | Radmacher |
| 2003/0032638 A1 | 2/2003 | Kim et al. |
| 2003/0049025 A1 | 3/2003 | Neumann |
| 2003/0051728 A1 | 3/2003 | Lloyd et al. |
| 2003/0070738 A1 | 4/2003 | Hamilton |
| 2003/0118512 A1 | 6/2003 | Shen |
| 2003/0121906 A1 | 7/2003 | Abbott |
| 2003/0131843 A1 | 7/2003 | Lu |
| 2003/0138508 A1 | 7/2003 | Novack et al. |
| 2003/0145924 A1 | 8/2003 | Carter, Jr. |
| 2004/0001048 A1 | 1/2004 | Kraus |
| 2004/0016427 A1 * | 1/2004 | Byron .................. A61M 11/041 128/200.14 |
| 2004/0035409 A1 | 2/2004 | Harwig |
| 2004/0055504 A1 | 3/2004 | Lee |
| 2004/0083919 A1 | 5/2004 | Hosey |
| 2004/0096402 A1 | 5/2004 | Hodges et al. |
| 2004/0099269 A1 | 5/2004 | Hale et al. |
| 2004/0101481 A1 | 5/2004 | Hale et al. |
| 2004/0102434 A1 | 5/2004 | Hale |
| 2004/0105818 A1 | 6/2004 | Every et al. |
| 2004/0162517 A1 | 8/2004 | Furst |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2006/0032496 A1 | 2/2006 | Hale et al. |
| 2006/0120962 A1 | 6/2006 | Rabinowitz et al. |
| 2006/0148970 A1 | 7/2006 | Kuba |
| 2006/0193788 A1 | 8/2006 | Hale et al. |

(56) References Cited

U.S. PATENT DOCUMENTS

| | | | |
|---|---|---|---|
| 2006/0257329 | A1 | 11/2006 | Rabinowitz et al. |
| 2007/0122353 | A1* | 5/2007 | Hale ............... A61K 9/0078 424/46 |
| 2007/0286816 | A1 | 12/2007 | Hale et al. |
| 2008/0038363 | A1 | 2/2008 | Zaffaroni et al. |
| 2008/0210225 | A1* | 9/2008 | Geiger ............ A61M 15/0086 128/200.14 |
| 2008/0216828 | A1 | 9/2008 | Wensley |
| 2008/0257345 | A1* | 10/2008 | Snyder ............ A61M 15/0086 128/203.15 |
| 2008/0299048 | A1 | 12/2008 | Hale et al. |
| 2008/0306285 | A1 | 12/2008 | Hale et al. |
| 2008/0311176 | A1 | 12/2008 | Hale |
| 2009/0062254 | A1 | 3/2009 | Hale et al. |
| 2009/0180968 | A1 | 7/2009 | Hale et al. |
| 2009/0229600 | A1 | 9/2009 | Hale |
| 2009/0235926 | A1 | 9/2009 | Cross |
| 2009/0246147 | A1 | 10/2009 | Rabinowitz |
| 2009/0258075 | A1 | 10/2009 | Hale |
| 2009/0301363 | A1 | 12/2009 | Damani |
| 2010/0006092 | A1 | 1/2010 | Hale et al. |
| 2010/0055048 | A1 | 3/2010 | Hale et al. |
| 2010/0065052 | A1 | 3/2010 | Sharma et al. |
| 2010/0068155 | A1 | 3/2010 | Lei et al. |
| 2010/0181387 | A1 | 7/2010 | Zaffaroni et al. |
| 2010/0208438 | A1 | 8/2010 | Kaltenbacher |
| 2010/0294268 | A1 | 11/2010 | Wensley et al. |
| 2010/0300433 | A1 | 12/2010 | Sharma et al. |
| 2011/0233043 | A1 | 9/2011 | Cross et al. |
| 2011/0240013 | A1 | 10/2011 | Hale et al. |
| 2011/0240014 | A1 | 10/2011 | Bennett et al. |
| 2011/0240022 | A1 | 10/2011 | Hodges et al. |
| 2011/0244020 | A1 | 10/2011 | Hale et al. |
| 2011/0245493 | A1 | 10/2011 | Rabinowitz et al. |
| 2011/0253135 | A1 | 10/2011 | Hale et al. |
| 2012/0048963 | A1 | 3/2012 | Sharma et al. |
| 2013/0032139 | A1 | 2/2013 | Hale et al. |
| 2013/0180525 | A1 | 7/2013 | Cross et al. |
| 2014/0060525 | A1 | 3/2014 | Hale et al. |
| 2014/0060532 | A1 | 3/2014 | Hodges |
| 2014/0066618 | A1 | 3/2014 | Hale et al. |
| 2014/0072605 | A1 | 3/2014 | Bennett et al. |
| 2015/0157635 | A1 | 6/2015 | Hale et al. |
| 2015/0250800 | A1 | 9/2015 | Hale et al. |
| 2015/0265783 | A1 | 9/2015 | Damani et al. |
| 2016/0166564 | A1 | 6/2016 | Myers et al. |
| 2016/0324845 | A1 | 11/2016 | Myers et al. |
| 2016/0374937 | A1 | 12/2016 | Hale et al. |
| 2017/0049974 | A1 | 2/2017 | Wensley et al. |
| 2017/0105246 | A1 | 4/2017 | Cross et al. |
| 2017/0281884 | A1 | 10/2017 | Hodges et al. |
| 2018/0021328 | A1 | 1/2018 | Myers et al. |
| 2018/0126098 | A1 | 5/2018 | Sharma et al. |
| 2019/0021987 | A1 | 1/2019 | Sharma |
| 2019/0117909 | A1 | 4/2019 | Myers |
| 2019/0209546 | A1 | 7/2019 | Myers |
| 2019/0307680 | A1 | 10/2019 | Cassella |
| 2020/0246559 | A1 | 8/2020 | Wensley |
| 2021/0008300 | A1 | 1/2021 | Sharma |
| 2021/0046259 | A1 | 2/2021 | Hasegawa |
| 2021/0052830 | A1 | 2/2021 | Myers |

FOREIGN PATENT DOCUMENTS

| | | |
|---|---|---|
| CN | 1700934 A | 11/2005 |
| CN | 1990057 A | 7/2007 |
| DE | 3542447 A1 | 6/1987 |
| EP | 0277519 | 8/1988 |
| EP | 279796 A1 | 8/1988 |
| EP | 0358114 | 3/1990 |
| EP | 0430559 | 6/1991 |
| EP | 816674 A1 | 1/1998 |
| GB | 2049651 A | 12/1980 |
| JP | 2006-523486 | 10/2006 |
| KR | 10-2217768 | 2/2021 | |
| WO | WO-9311817 A1 * | 6/1993 | ........ A61M 15/0086 |
| WO | WO 1994/009842 | 5/1994 | |
| WO | WO 1994/027653 | 12/1994 | |
| WO | WO 1996/009846 | 4/1996 | |
| WO | WO 1996/013161 | 5/1996 | |
| WO | WO 1996/013290 | 5/1996 | |
| WO | WO 1996/013291 | 5/1996 | |
| WO | WO 1996/013292 | 5/1996 | |
| WO | WO 1996/030068 | 10/1996 | |
| WO | WO 1997/027804 | 8/1997 | |
| WO | WO 1998/022170 | 5/1998 | |
| WO | WO 1998/036651 | 8/1998 | |
| WO | WO 1999/064094 | 12/1999 | |
| WO | WO 2000/029053 | 5/2000 | |
| WO | WO 2000/066084 | 11/2000 | |
| WO | WO 2000/066206 | 11/2000 | |
| WO | WO 2000/076673 | 12/2000 | |
| WO | WO 2001/005459 | 1/2001 | |
| WO | WO 2002/094218 | 11/2002 | |
| WO | WO 2002/094236 | 11/2002 | |
| WO | WO 2002/094242 | 11/2002 | |
| WO | WO 2003/037412 | 5/2003 | |
| WO | WO 2003/094900 | 11/2003 | |
| WO | WO 2003/095012 | 11/2003 | |
| WO | 2004/091704 | 10/2004 | |
| WO | WO 2004/104490 | 12/2004 | |
| WO | WO 2004/104491 | 12/2004 | |
| WO | WO 2004/104492 | 12/2004 | |
| WO | WO 2004/104493 | 12/2004 | |
| WO | WO 2004/106268 | 12/2004 | |
| WO | WO 2005/120614 | 12/2005 | |
| WO | WO 2012/026963 | 3/2012 | |
| WO | 2016/145075 | 9/2016 | |

OTHER PUBLICATIONS

European Supplementary Search Report for Application No. EP 16762425, dated Oct. 26, 2018, 3 pages.
Examination report for Australian Application No. 2016229119, dated Nov. 13, 2017, 4 pages.
Examination report for Canadian Application No. 2,979,213, dated Jun. 22, 2018, 7 pages.
First Examination report for New Zealand Application No. 735414, dated Mar. 19, 2018, 7 pages.
Further Examination Report for New Zealand Application No. 735414, dated Nov. 6, 2018, 3 pages.
International Preliminary Report on Patentability for PCT/US2016/021554, dated Sep. 12, 2017, 7 pages.
International Search Report and the Written Opinion of the International Searching Authority for PCT/US2016/021554, dated May 27, 2016, 11 pages.
Japanese Office Action with English translation for Japanese Application No. 2017-548052, dated Oct. 29, 2018.
U.S. Appl. No. 13/311,660, filed Dec. 6, 2011, Bennett et al.
U.S. Appl. No. 13/597,865, filed Aug. 29, 2012, Bennett et al.
Communication pursuant to Article 94(3) EPC for Application No. 16762425.3, dated Oct. 23, 2019, 8 pages.
Examination report for Australia Application No. 2018264013, dated Feb. 20, 2020, 4 pages.
Office Action issued for Canada Application No. 2,979,213, dated Apr. 2, 2019, 5 pages.
Office Action issued for Canada Application No. 2,979,213, dated Feb. 3, 2020, 5 pages.
Office Action issued for China Application No. 201680027355.7, dated Nov. 29, 2019, along with English translation, 15 pages.
Office Action for Japan Application No. 2017-548052, dated Sep. 20, 2019, along with English translation, 6 pages.
Office Action for Korea Application No. 10-2017-7028542, dated Jan. 21, 2019, along with English translation, 15 pages.
U.S. Appl. No. 12/628,949, filed Dec. 1, 2009, Zaffaroni.
U.S. Appl. No. 13/078,516, filed Apr. 1, 2011, Hale.
U.S. Appl. No. 13/078,519, filed Apr. 1, 2011, Hale.
U.S. Appl. No. 13/078,525, filed Apr. 1, 2011, Rainbow.
U.S. Appl. No. 13/078,600, filed Apr. 1, 2011, Hodges.

(56) References Cited

OTHER PUBLICATIONS

U.S. Appl. No. 13/078,606, filed Apr. 1, 2011, Hale.
U.S. Appl. No. 13/078,654, filed Apr. 1, 2011, Cross.
U.S. Appl. No. 13/078,668, filed Apr. 1, 2011, Bennett.
U.S. Appl. No. 13/217,385, filed Aug. 25, 2011, Sharma.
Banhart (2000) JOM 12:22-27 "Manufacturing Routes for Metallic Foams."
Banhart (2001) Progress in Materials Science, 46:559-632 "Manufacture, characterization and application of cellular metals and metal foams."
Bennett et al. (1981) Annual Surg. 195(6):700-705 "Patient-Controlled Analgesia: A New Concept of Postoperative Pain Relief."
Bickes and Grubelich (1996) "SCB Ignitioin of Pyrotechnics, thermites, and intermetallics". Explosive Components Department, Sandia National Laboratories. Aug. 20, 1996.
Communication pursuant to Article 94(3) EPC from European App No. 16762425.3, dated Dec. 3, 2020, 6 pages.
Darquenne et al. (1997) American Physiological Society 83(3):966-974, "Aerosol Dispersion in Human Lung: Comparison Between Numerical Simulations and Experiments for Bolus Tests."
Davies et al. (1972) Journal of Applied Physiology 32(5):591-600, "Breathing of Half-Micron Aerosols."
Dershwitz et al. (2000) Anesthesiology 93(3): 619-628 "Pharmacokinetics and Pharmacodynamics of Inhaled versus Intravenous Morphine in Healthy Volunteers."
De Yong et al. (1998) Propellants, Explosives, Pyrotechnics 23:328-332 "Radiative Ignition of Pyrotechnics: Effect of Wavelength on Ignition Threshold."
Finlay (2001) "The Mechanics of Inhaled Pharmaceutical Aerosols", Academic Press: San Diego Formula 2.39. pp. 3-14 (Table of Contents). pp. v-viii.
Frieser et al. (1980) Journal of Applied Electrochemistry 10:449-457 "Surface treatments of silicon to enhance thermal nucleation."
Gonda (1991) "Particle Deposition in the Human Respiratory Tract," Chapter 176, The Lung: Scientific Foundations. Crystal R.G.and West, J.B. (eds.), Raven Publishers, New York. pp. 2289-2294.
Heyder et al. (1986) J. Aerosol Sci. 17(5):811-822 "Deposition of Particles in the Human Respiratory Tract in the Size Range 0.005-15 μm."
Hurt and Robertson (1998) JAMA 280(13):1173-1181 "Prying Open the Door to the Tobacco Industry's Secrets About Nicotine: The Minnesota Tobacco Trial."
International Search Report and Written Opinion for PCT/US2016/021554, dated May 27, 2016.
Martin and Lue (May/Jun. 1989) Journal of Analytical Toxicology 13:158-162 "Pyrolysis and Volatilization of Cocaine."
McCarthy et al. (May 1985) Sandia Report "Burn Front Velocity as a function of Pellet Density in Iron /Potassium Perchlorate Heat Powders."
Merzhanov, Alexander G., (Aug. 19, 1994) Russian Academy of Sciences: International Pyrotechnics Seminar Colorado Springs, US Jul. 25-29, 1994 "Pyrotechnical Aspects of Self-Propogating High-Temperature Synthesis."
Office Action dated Jun. 22, 2018 with respect to Canadian App No. 2,979,213, 7 pages.
Office Action dated Sep. 10, 2020 with respect to Chinese App No. 201680027355.7 (w/English Translation).
Office Action dated Oct. 31, 2019 with respect to Korean App No. 10-2017-7028542 (w/English Translation) 13 pages.
Office Action dated Apr. 30, 2021 with respect to Korean App No. 10-2021-7004329 (w/English Translation), 6 pages.
Office Action dated May 3, 2021 with respect to New Zealand App No. 754325, 4 pages.
Office Action dated May 11, 2021 with respect to New Zealand App No. 751850, 5 pages.

Pankow et al. (1997) Environ. Sci. Technol. 31:2428-2433 "Conversion of Nicotine in Tobacco Smoke to Its Volatile and Available Free-Base Form through the Action of Gaseous Ammonia."
Pankow (2000) ACS Conference—San Francisco—Mar. 26, 2000, pp. 1-8 "Chemistry of Tobacco Smoke."
Peeters et al. (Jul. 1997) Circuits and Devices pp. 19-23 "Thermal Inkjet Technology."
Reticulated Vitreous Carbon (1997) Flyer for ERG Materials and Aerospace Corp.
Seeman et al. (1999) J. Agric. Food Chem. 47(12):5133-5145 "The Form of Nicotine in Tobacco. Thermal Transfer of Nicotine and Nicotine Acid Salts to Nicotine in the Gas Phase."
Sekine and Nakahara (1987) Journal of Forensic Science 32(5):1271-1280 "Abuse of Smoking Methamphetamine Mixed with Tobacco: 1. Inhalation Efficiency and Pyrolysis Products of Methamphetamine."
Supplementary Search Report for European App No. 16762425, dated Oct. 26, 2018, 3 pages.
Ward et al. (1997) Clinical Pharmacology & Therapeutics 62(6):596-609 "Morphine Pharmacokinetics after Pulmonary Administration from a Novel Aerosol Deliveiy System."
Bickes and Grubelich (1996) "SCB Ignition of Pyrotechnics, thermites, and intermetallics". Explosive Components Department, Sandia National Laboratories. Aug. 20, 1996.
Office Action dated Jun. 13, 2022 with respect to China App No. 202110917521.3 (w/English Translation), 8 pages.
Office Action dated Nov. 28, 2019 with respect to Israel App No. 254407 (w/ English Summary), 6 pages.
Office Action dated Jan. 24, 2021 with respect to Israel App No. 254407 (w/ English Summary), 8 pages.
Office Action dated May 17, 2022 with respect to Japan App No. 2020-166796 (w/English Translation), 6 pages.
Communication pursuant to Article 94(3) EPC from European App No. 16762425.3, dated Jul. 20, 2021, 6 pages.
Examination report 2 for Australia Application No. 2018264013, dated Nov. 16, 2020, 3 pages.
Examination report 3 for Australia Application No. 2018264013, dated Feb. 5, 2021, 4 pages.
Examination report 4 for Australia Application No. 2018264013, dated Feb. 17, 2021, 5 pages.
Examination report 5 for Australia Application No. 2018264013, dated Feb. 19, 2021, 6 pages.
Examination Report 1 for Australia Application No. 2021201111, dated Apr. 27, 2022; 5 pages.
Examination Report 1 for New Zealand App No. 751850, dated Jul. 20, 2020, 4 pages.
Examination Report 2 for New Zealand App No. 751850, dated Nov. 18, 2020, 4 pages.
Examination Report 3 for New Zealand App No. 751850, dated Mar. 18, 2021, 4 pages.
Office Action dated Dec. 2, 2020 with respect to Canadian App No. 2,979,213, 4 pages.
Office Action dated Aug. 4, 2021 with respect to Canadian App No. 2,979,213, 5 pages.
Office Action dated Apr. 4, 2022 with respect to Canadian App No. 2,979,213, 4 pages.
Office Action dated Apr. 15, 2021 with respect to Chinese App No. 201680027355.7 (w/ English Translation), 12 pages.
Office Action dated Sep. 9, 2021 with respect to Chinese App No. 201680027355.7 (w/ English Translation), 4 pages.
Office Action dated Feb. 22, 2022 with respect to Chinese App No. 202110917521.3 (w/ English Translation), 11 pages.
Office Action dated Oct. 1, 2021 with respect to Japanese App No. 2020-166796 (w/ English Translation), 6 pages.
Office Action dated Apr. 28, 2022 with respect to Mexico App No. MX/a/2017/011613 (w/English Summary), 4 pages.

* cited by examiner

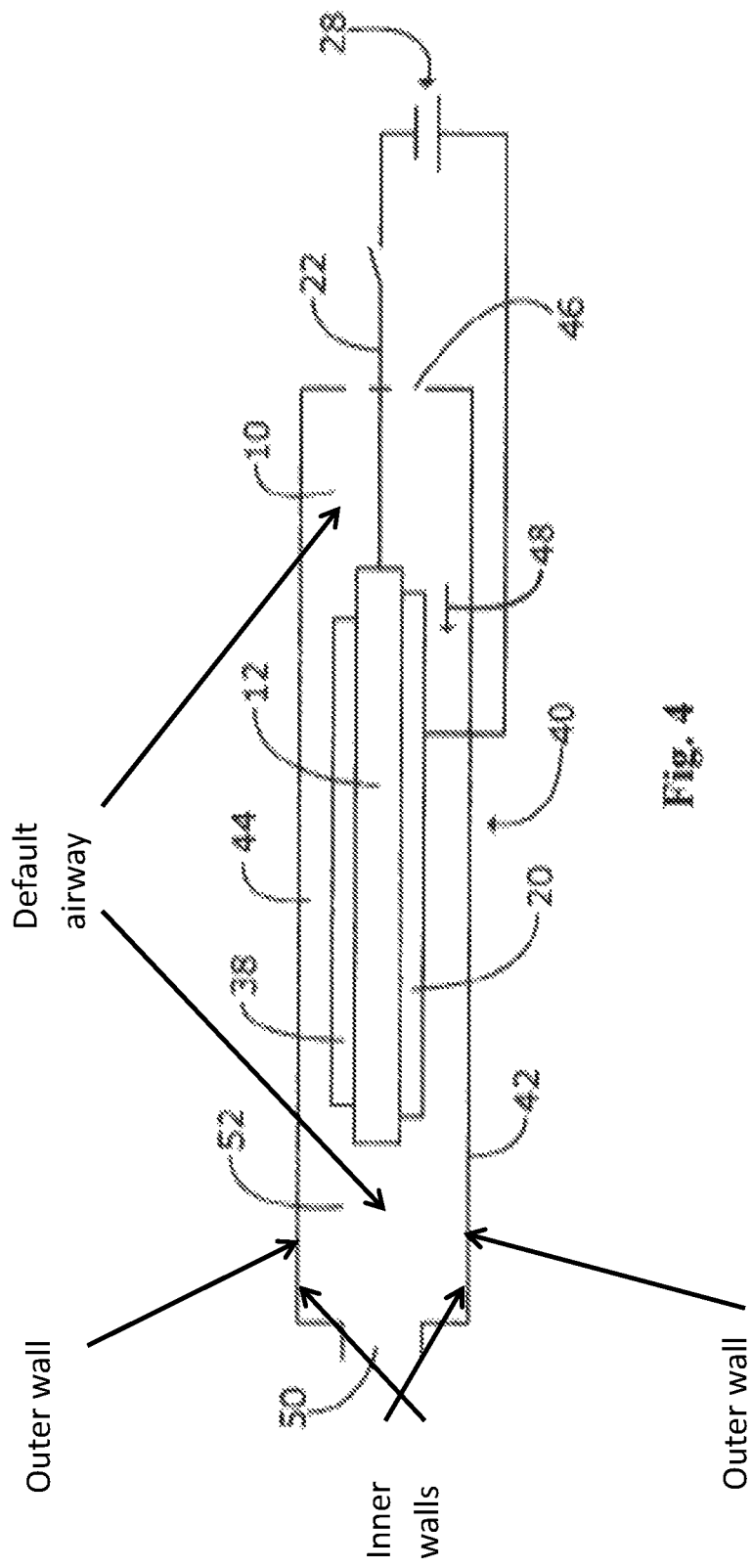

USE OF ANTISTATIC MATERIALS IN THE AIRWAY FOR THERMAL AEROSOL CONDENSATION PROCESS

CROSS-REFERENCE TO RELATED APPLICATION

This application claims priority to and is a 35 U.S.C. § 371 national phase application of PCT/US2016/021554 (WO2016/145075), filed on Mar. 9, 2016 entitled "Use of Antistatic Materials in the Airway for Thermal Aerosol Condensation Process", which application claims priority to U.S. provisional application Ser. No. 62/131,823, filed on Mar. 11, 2015 entitled "Use of Antistatic Materials in the Airway for Thermal Aerosol Condensation Process". The entire disclosures of which are hereby incorporated by reference. Any disclaimer that may have occurred during the prosecution of the above-referenced applications is hereby expressly rescinded, and reconsideration of all relevant art is respectfully requested.

FIELD OF THE INVENTION

This invention relates to materials utilized in devices for delivery of an aerosol through an inhalation route. Specifically, the present invention relates to the use of antistatic materials in devices for producing aerosols containing active drugs that are used in inhalation therapy.

BACKGROUND

Currently, there are a number of approved devices for the inhalation delivery of drugs, including dry powder inhalers, nebulizers, and pressurized metered dose inhalers. The aerosols produced by the devices, however, typically contain an excipient.

Rapid vaporization of thin films of drugs at temperatures up to 600° C. in less than 500 msec in an air flow can produce drug aerosols having high yield and high purity with minimal degradation of the drug. Condensation drug aerosols can be used for effective pulmonary delivery of drugs using inhalation medical devices. Devices and methods in which thin films of drugs deposited on metal substrates are vaporized by electrically resistive heating have been demonstrated. Chemically-based heat packages which can include a fuel capable of undergoing an exothermic metal oxidation-reduction reaction within an enclosure can also be used to produce a rapid thermal impulse capable of vaporizing thin films to produce high purity aerosols, as disclosed, for example in U.S. application Ser. No. 10/850,895 entitled "Self-Contained heating Unit and Drug-Supply Unit Employing Same" filed May 20, 2004, and U.S. application Ser. No. 10/851,883, entitled "Percussively Ignited or Electrically Ignited Self-Contained Heating Unit and Drug Supply Unit Employing Same," filed May 20, 2004, the entirety of both of which are herein incorporated by reference. These devices and methods are appropriate for use with compounds that can be deposited as physically and chemically stable solids.

Aerosols from MDIs and DPIs are often highly charged, which can lead to inconsistent aerosol output and potentially impact therapeutic effects. For example, Pidrart et. al. discovered ~14% aerosol particles loss in a MDI spacer due to charges. One factor that can affect drug output from the inhaler is electrostatic interaction between charged drug aerosol particles and the device components surrounding the aerosol.

The embodiments disclosed herein are directed toward overcoming one or more of the problems discussed above.

SUMMARY OF THE EMBODIMENTS

The disclosure teaches the use of antistatic materials in the airway for thermal aerosol generation devices. The present disclosure teaches the use of antistatic materials for drug delivery in any drug that may be susceptible to charging during aerosol generation, for example, Alprazolam. A number of possible embodiments of the disclosure include both airway materials which are antistatic as well as coatings for the airway. The disclosure teaches metallized airways (produced by coating the inner wall of the airway with conductive metals such as stainless steel/copper/copper/stainless steel, or by applying a metallic tape (like copper) to the inner and outer walls of the airway), the use of an antistatic spray (such as the Staticide brand) on the default airway, and the use of antistatic plastics (such as the Permastat or Permastat plus brands) as airway materials.

The disclosure teaches drug aerosols formed using a thermal aerosol condensation method. In one embodiment of this technology involves a drug-coated substrate placed inside an airway. For certain drugs, such as Alprazolam, the aerosol formed can have a tendency to variably deposit on the airway, leading to a lowered and inconsistent emitted dose. Certain drugs form a charged aerosol upon vaporization in certain conditions. The charged aerosol can deposit on the airway by electrostatic attraction. The disclosure teaches the use of the anti-static treatment for reduction in aerosol charging and airway deposition.

The disclosure teaches a method and apparatus for providing inhalation delivery of a drug wherein the emitted dose of the drug aerosol formed by thermal aerosol condensation yields more consistent dosing with the use of antistatic materials in the airway than the emitted dose of the drug aerosol formed by thermal aerosol condensation without the use of antistatic materials in the airway. The use of the anti-static material significantly reduces the amount of drug aerosol deposited on the airway. The use of anti-static material reduces the charge on the aerosol. The method and apparatus achieves drug delivery of drugs characterized by drugs that form a charged aerosol upon vaporization.

BRIEF DESCRIPTION OF THE DRAWINGS

FIG. 4 is a schematic representation of a drug delivery device.

DETAILED DESCRIPTION OF THE EMBODIMENTS

Figure 1:
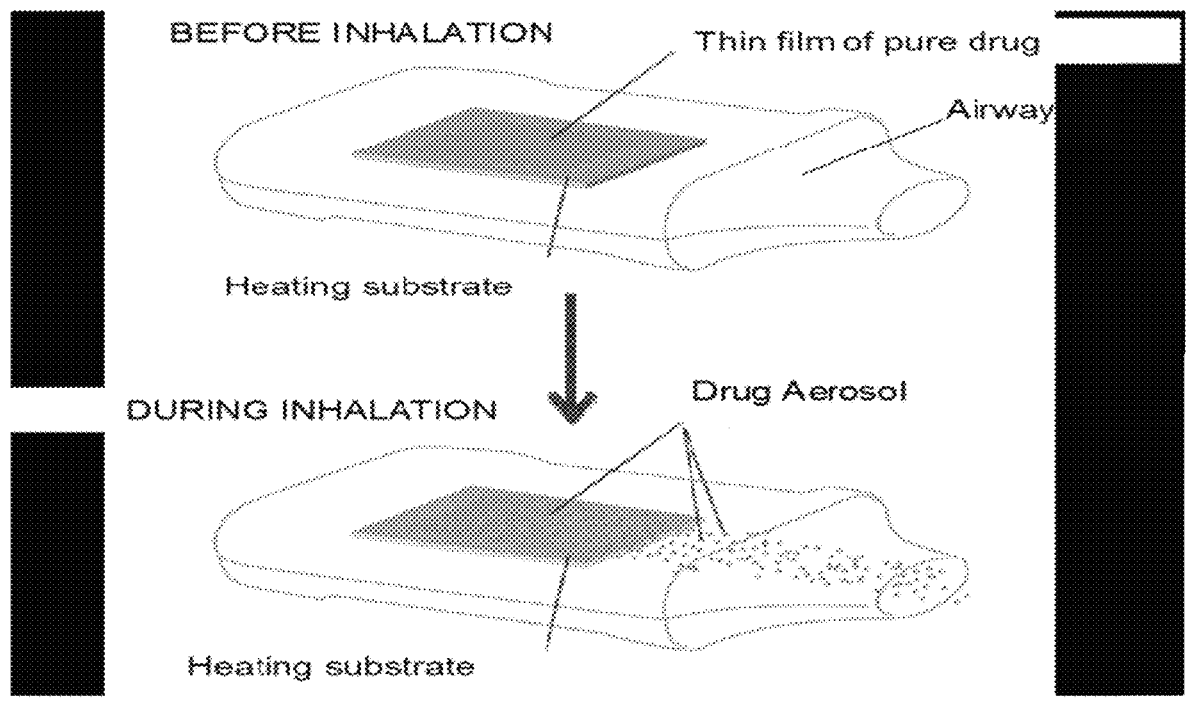
FIG. 1 shows the Staccato single dose device.

As defined herein, the following terms shall have the following meanings when reference is made to them throughout the specification.

"Aerodynamic diameter" of a given particle refers to the diameter of a spherical droplet with a density of 1 g/mL (the density of water) that has the same settling velocity as the given particle.

"Aerosol" refers to a collection of solid or liquid particles suspended in a gas.

"Aerosol mass concentration" refers to the mass of particulate matter per unit volume of aerosol.

Antistatic material include, but are not limited to, airway materials which are antistatic as well as coatings for the airway. These antistatic material includes metallized airways (produced by coating the inner wall of the airway with conductive metals such as stainless steel/copper/copper/stainless steel, and/or by applying a metallic tape (like copper) to the inner and outer walls of the airway), the use of an antistatic spray (such as the Staticide brand) on the default airway, and/or the use of antistatic plastics (such as the Permastat or Permastat plus brands) as air way materials. Materials with antistatic properties are included in this disclosure.

"Condensation aerosol" refers to an aerosol that has been formed by the vaporization of a composition and subsequent cooling of the vapor, such that the vapor condenses to form particles.

"Decomposition index" refers to a number derived from an assay. The number is determined by subtracting the purity of the generated aerosol, expressed as a fraction, from 1.

"Drug" means any substance that is used in the prevention, diagnosis, alleviation, treatment or cure of a condition. The drug is preferably in a form suitable for thermal vapor delivery, such as an ester, free acid, or free base form. The terms "drug", "compound", and "medication" are used herein interchangeably. As described in throughout the specification, the term drug includes nicotine and nicotine meta-salicylate.

"Drug composition" refers to a composition that comprises only pure drug, two or more drugs in combination, or one or more drugs in combination with additional components. Additional components can include, for example, pharmaceutically acceptable excipients, carriers, and surfactants.

"Drug degradation product" or "thermal degradation product" are used interchangeably and means any byproduct, which results from heating the drug(s) and is not responsible for producing a therapeutic effect.

"Drug supply article" or "drug supply unit" are used interchangeably and refers to a substrate with at least a portion of its surface coated with one or more drug compositions. Drug supply articles of the invention may also include additional elements such as, for example, but not limitation, a heating element.

"Fraction drug degradation product" refers to the quantity of drug degradation products present in the aerosol particles divided by the quantity of drug plus drug degradation product present in the aerosol, i.e. (sum of quantities of all drug degradation products present in the aerosol)/((quantity of drug(s) present in the aerosol)+(sum of quantities of all drug degradation products present in the aerosol)). The term "percent drug degradation product" as used herein refers to the fraction drug degradation product multiplied by 100%, whereas "purity" of the aerosol refers to 100% minus the percent drug degradation products.

"Heat stable drug" refers to a drug that has a TSR≥9 when vaporized from a film of some thickness between 0.05 µm and 20 µm.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Number concentration" refers to the number of particles per unit volume of aerosol.

"Purity" as used herein, with respect to the aerosol purity, means the fraction of drug composition in the aerosol/the fraction of drug composition in the aerosol plus drug degradation products. Thus purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

"Settling velocity" refers to the terminal velocity of an aerosol particle undergoing gravitational settling in air.

"Support" refers to a material on which the composition is adhered, typically as a coating or thin film. The term "support" and "substrate" are used herein interchangeably.

"Substantially free of" means that the material, compound, aerosol, etc., being described is at least 95% free of the other component from which it is substantially free.

"Typical patient tidal volume" refers to 1 L for an adult patient and 15 mL/kg for a pediatric patient.

"Therapeutically effective amount" means the amount required to achieve a therapeutic effect. The therapeutic effect could be any therapeutic effect ranging from prevention, symptom amelioration, symptom treatment, to disease termination or cure.

"Thermal stability ratio" or "TSR" means the % purity/(100%-% purity) if the % purity is <99.9%, and 1000 if the % purity is ≥99.9%. For example, a respiratory drug vaporizing at 90% purity would have a TSR of 9.

"4 µm thermal stability ratio" or "4TSR" means the TSR of a drug determined by heating a drug-comprising film of about 4 microns in thickness under conditions sufficient to vaporize at least 50% of the drug in the film, collecting the resulting aerosol, determining the purity of the aerosol, and using the purity to compute the TSR. In such vaporization, generally the about 4-micron thick drug film is heated to around 350° C. but not less than 200° C. for around 1 second to vaporize at least 50% of the drug in the film.

"1.5 µm thermal stability ratio" or "1.5TSR" means the TSR of a drug determined by heating a drug-comprising film of about 1.5 microns in thickness under conditions sufficient to vaporize at least 50% of the drug in the film, collecting the resulting aerosol, determining the purity of the aerosol, and using the purity to compute the TSR. In such vaporization, generally the about 1.5-micron thick drug film is heated to around 350° C. but not less than 200° C. for around 1 second to vaporize at least 50% of the drug in the film.

"0.5 µm thermal stability ratio" or "0.5TSR" means the TSR of a drug determined by heating a drug-comprising film of about 0.5 microns in thickness under conditions sufficient to vaporize at least 50% of the drug in the film, collecting the resulting aerosol, determining the purity of the aerosol, and using the purity to compute the TSR. In such vaporization, generally the about 0.5-micron thick drug film is heated to around 350° C. but not less than 200° C. for around 1 second to vaporize at least 50% of the drug in the film.

"Vapor" refers to a gas, and "vapor phase" refers to a gas phase. The term "thermal vapor" refers to a vapor phase, aerosol, or mixture of aerosol-vapor phases, formed preferably by heating.

When a condensation aerosol is formed in an airflow, a certain portion of the aerosol can deposit on downstream physical features such as the side walls of the airway defining the airflow, the mouthpiece of the device, or other structures and thereby reduce the amount of active compound emitted by the device and available for administration. For many treatment regimens, the ability to deliver a dose comprising a precise, consistent, and reproducible amount of a physiologically active compound can impact the therapeutic efficacy of the treatment regimens, and in some cases, such a capability can also enable new therapies. Thus, there is a need for inhalation devices and methods of producing a condensation aerosol that can deliver precise, reproducible and/or controlled amounts of a physiologically active substance. This disclosure teaches the use of antistatic materials in the airway for thermal aerosol generation devices. The present disclosure teaches the use of antistatic materials for drug delivery in any drug that may be susceptible to charging during aerosol generation, for example, Alprazolam. A number of possible embodiments of the disclosure include both airway materials which are antistatic as well as coatings for the airway. The disclosure teaches metallized airways (produced by coating the inner wall of the airway with conductive metals such as stainless steel/copper/copper/stainless steel, or by applying a metallic tape (like copper) to the inner and outer walls of the airway), the use of an antistatic spray (such as the Staticide brand) on the default airway, and the use of antistatic plastics (such as the Permastat or Permastat plus brands) as air way materials.

Aerosol Composition

The compositions described herein typically comprise drug compounds. The compositions may comprise other compounds as well. For example, the composition may comprise a mixture of drug compounds and a pharmaceutically acceptable excipient, or a mixture of a drug compound with other compounds having useful or desirable properties. The composition may comprise a pure drug compound as well. In one embodiment, the composition consists essentially of pure drug and contains no propellants or solvents.

Additionally, pharmaceutically acceptable carriers, surfactants, enhancers, and inorganic compounds may be included in the composition. Examples of such materials are known in the art.

In some variations, the aerosols are substantially free of organic solvents and propellants. Additionally, water is typically not added as a solvent for the nicotine metasalicylate, although water from the atmosphere may be incorporated in the aerosol during formation, in particular, while passing air over the film and during the cooling process. In other variations, the aerosols are completely devoid of organic solvents and propellants. In yet other variations, the aerosols are completely devoid of organic solvents, propellants, and any excipients. These aerosols comprise only pure drug, less than 10% drug degradation products, and a carrier gas, which is typically air.

Typically, the drug has a decomposition index less than 0.15. Preferably, the drug has a decomposition index less than 0.10. More preferably, the drug has a decomposition index less than 0.05. Most preferably, the drug has a decomposition index less than 0.025

In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations, the condensation aerosol particles comprise less than 10% by weight of a thermal degradation product. In other variations, the condensation drug aerosol particles comprise less than 5%, 1%, 0.5%, 0.1%, or 0.03% by weight of a thermal degradation product.

In certain embodiments of the disclosure, the drug aerosol has a purity of between 90% and 99.8%, or between 93% and 99.7%, or between 95% and 99.5%, or between 96.5% and 99.2%. In certain embodiments of the disclosure, the drug aerosol has percent of freebase nicotine in the aerosol of between 90% and 99.8%, or between 93% and 99.7%, or between 95% and 99.5%, or between 96.5% and 99.2%.

Typically, the aerosol has a number concentration greater than $10^6$ particles/mL. In other variations, the aerosol has a number concentration greater than $10^7$ particles/mL. In yet other variations, the aerosol has a number concentration greater than $10^8$ particles/mL, greater than $10^9$ particles/mL, greater than $10^{10}$ particles/mL, or greater than $10^{11}$ particles/mL.

The gas of the aerosol typically is air. Other gases, however, can be used, in particular inert gases, such as argon, nitrogen, helium, and the like. The gas can also include vapor of the composition that has not yet condensed to form particles. Typically, the gas does not include propellants or vaporized organic solvents. In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations the condensation drug aerosol has a MMAD in the range of about 0.01-3 μm. In some variations the condensation drug aerosol has a MMAD in the range of about 0.1-3 μm. In some variations the geometric standard deviation around the MMAD of the condensation drug aerosol particles is less than 3.0. In other variations, the geometric standard deviation around the MMAD of the condensation drug aerosol particles is less than 2.5, or less than 2.0.

In certain embodiments of the invention, the drug aerosol comprises one or more drugs having a 4TSR of at least 5 or 10, a 1.5TSR of at least 7 or 14, or a 0.5TSR of at least 9 or 18. In other embodiments of the invention, the drug aerosol comprises one or more drugs having a 4TSR of between 5 and 100 or between 10 and 50, a 1.5TSR of between 7 and 200 or between 14 and 100, or a 0.5TSR of between 9 and 900 or between 18 and 300.

Formation of Condensation Aerosols

Any suitable method may be used to form the condensation aerosols described herein. One such method involves the heating of a composition to form a vapor, followed by cooling of the vapor so that it forms an aerosol (i.e., a condensation aerosol). Methods have been previously described in U.S. Pat. No. 7,090,830. This reference is hereby incorporated by reference in its entirety.

Typically, the composition is coated on a substrate, and then the substrate is heated to vaporize the composition. The substrate may be of any geometry and be of a variety of different sizes. It is often desirable that the substrate provide a large surface to volume ratio (e.g., greater than 100 per meter) and a large surface to mass ratio (e.g., greater than 1 $cm^2$ per gram). The substrate can have more than one surface A substrate of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials may be used to construct the substrate. Typically, the substrates are heat-conductive and include metals, such as aluminum, iron, copper, stainless steel, and the like, alloys, ceramics, and filled polymers. In one variation, the substrate is stainless steel. Combinations of materials and coated variants of materials may be used as well.

When it is desirable to use aluminum as a substrate, aluminum foil is a suitable material. Examples of alumina and silicon based materials BCR171 (an alumina of defined surface area greater than 2 $m^2/g$ from Aldrich, St. Louis, Mo.) and a silicon wafer as used in the semiconductor industry.

Typically it is desirable that the substrate have relatively few, or substantially no, surface irregularities. Although a variety of supports may be used, supports that have an impermeable surface, or an impermeable surface coating, are typically desirable. Illustrative examples of such supports include metal foils, smooth metal surfaces, nonporous ceramics, and the like. Alternatively, or in addition, to preferred substrates having an impermeable surface, the substrate surface expanse is characterized by a contiguous surface area of about 20 $mm^2$. Alternatively, or in addition, to preferred substrates having an impermeable surface, the substrate surface expanse is characterized by a contiguous surface area of greater than 1 $mm^2$, preferably 10 $mm^2$, more preferable 50 $mm^2$ and still more preferably 100 $mm^2$, and a material density of greater than 0.5 g/cc. In contrast, non-preferred substrates typically have a substrate density of less than 0.5 g/cc, such as, for example, yarn, felts and foam, or have a surface area of less than 1 $mm^2$/particle such as, for example small alumina particles, and other inorganic particles, as it is difficult on these types of surfaces to generate therapeutic quantities of a drug aerosol with less than 10% drug degradation via vaporization.

In one variation, the disclosure teaches a stainless steel foil substrate. A hollow, stainless steel tube may be used as the drug-film substrate. In other variations, aluminum foil is used as a substrate for testing drug.

The composition is typically coated on the solid support in the form of a film. The film may be coated on the solid support using any suitable method. The method suitable for coating is often dependent upon the physical properties of the compound and the desired film thickness. One exemplary method of coating a composition on a solid support is by preparing a solution of compound (alone or in combination with other desirable compounds) in a suitable solvent, applying the solution to the exterior surface of the solid support, and then removing the solvent (e.g., via evaporation, etc.) thereby leaving a film on the support surface.

Common solvents include methanol, dichloromethane, methyl ethyl ketone, diethyl ether, acetone, ethanol, isopropyl alcohol, 3:1 chloroform:methanol mixture, 1:1 dichloromethane: methyl ethyl ketone mixture, dimethylformamide, and deionized water. In some instances (e.g., when triamterene is used), it is desirable to use a solvent such as formic acid. Sonication may also be used as necessary to dissolve the compound.

The composition may also be coated on the solid support by dipping the support into a composition solution, or by spraying, brushing or otherwise applying the solution to the support. Alternatively, a melt of the drug can be prepared and applied to the support. For drugs that are liquids at room temperature, thickening agents can be mixed with the drug to permit application of a solid drug film.

The film can be of varying thickness depending on the compound and the maximum amount of thermal degradation desired. In one method, the heating of the composition involves heating a thin film of the composition having a thickness between about 0.1 µm-30 µm to form a vapor. In yet other variations, the composition has a film thickness between about 0.5 µm-21 µm. Most typically, the film thickness vaporized is between 0.5 µm-25 µm.

The support on which the film of the composition is coated (12 in FIG. 4) can be heated by a variety of means to vaporize the composition. Exemplary methods of heating include the passage of current through an electrical resistance element, absorption of electromagnetic radiation (e.g., microwave or laser light) and exothermic chemical reactions (e.g., exothermic solvation, hydration of pyrophoric materials, and oxidation of combustible materials). Heating of the substrate by conductive heating is also suitable. One exemplary heating source is described in U.S. patent application for SELF-CONTAINED HEATING UNIT AND DRUG-SUPPLY UNIT EMPLOYING SAME, U.S. Ser. No. 60/472,697 filed May 21, 2003. The description of the exemplary heating source disclosed therein, is hereby incorporated by reference.

Heat sources (22 in FIG. 4) typically supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. Suitable heat sources include resistive heating devices which are supplied current at a rate sufficient to achieve rapid heating, e.g., to a substrate temperature of at least 200° C., 250° C., 300° C., or 350° C. preferably within 50-500 ms, more preferably in the range of 50-200 ms. Heat sources or devices that contain a chemically reactive material which undergoes an exothermic reaction upon actuation, e.g., by a spark or heat element, such as flashbulb type heaters of the type described in several examples, and the heating source described in the above-cited U.S. patent application for SELF-CONTAINED HEATING UNIT AND DRUG-SUPPLY UNIT EMPLOYING SAME, are also suitable. In particular, heat sources that generate heat by exothermic reaction, where the chemical "load" of the source is consumed in a period of between 50-500 msec or less are generally suitable, assuming good thermal coupling between the heat source and substrate.

When heating the thin film of the composition, to avoid decomposition, it is desirable that the vaporized compound should transition rapidly from the heated surface or surrounding heated gas to a cooler environment. This may be accomplished not only by the rapid heating of the substrate, but also by the use of a flow of gas across the surface of the substrate. While a vaporized compound from a surface may transition through Brownian motion or diffusion, the temporal duration of this transition may be impacted by the extent of the region of elevated temperature at the surface, which is established by the velocity gradient of gases over the surface and the physical shape of surface. Typical gas-flow rates used to minimize such decomposition and to generate a desired particle size are in the range of 1-10 L/minute.

The aerosol particles for administration can typically be formed using any of the describe methods at a rate of greater than $10^8$ inhalable particles per second. In some variations, the aerosol particles for administration are formed at a rate of greater than $10^9$ or $10^{10}$ inhalable particles per second. Similarly, with respect to aerosol formation (i.e., the mass of aerosolized particulate matter produced by a delivery device per unit time) the aerosol may be formed at a rate greater than 0.25 mg/second, greater than 0.5 mg/second, or greater than 1 or 2 mg/second. Further, with respect to aerosol formation, focusing on the drug aerosol formation rate (i.e., the rate of drug compound released in aerosol form by a delivery device per unit time), the drug may be aerosolized at a rate greater than 0.05 mg drug per second, greater than 0.1 mg drug per second, greater than 0.5 mg drug per second, or greater than 1 or 2 mg drug per second.

In some variations, the drug condensation aerosols are formed from compositions that provide at least 5% by weight of drug condensation aerosol particles. In other variations, the aerosols are formed from compositions that provide at least 10%, 20%, 30%, 40%, 50%, 60%, or 75% by weight of drug condensation aerosol particles. In still other variations, the aerosols are formed from compositions that provide at least 95%, 99%, or 99.5% by weight of drug condensation aerosol particles.

In some variations, the drug condensation aerosol particles when formed comprise less than 10% by weight of a thermal degradation product. In other variations, the drug condensation aerosol particles when formed comprise less than 5%, 1%, 0.5%, 0.1%, or 0.03% by weight of a thermal degradation product.

In some variations the drug condensation aerosols are produced in a gas stream at a rate such that the resultant aerosols have a MMAD in the range of about 0.1-3 µm. In some variations the geometric standard deviation around the MMAD of the drug condensation aerosol particles is less than 3.0. In other variations, the geometric standard deviation around the MMAD of the drug condensation aerosol particles is less than 2.5, or less than 2.0.

Delivery Devices

The delivery devices described herein for administering a condensation drug aerosol typically comprise an element for heating the composition to form a vapor and an element allowing the vapor to cool, thereby forming a condensation aerosol. These aerosols are generally delivered via inhalation to lungs of a patient, for local or systemic treatment. Alternatively, however, the condensation aerosols of the invention can be produced in an air stream, for application of drug-aerosol particles to a target site. For example, a stream of air carrying drug-aerosol particles can be applied to treat an acute or chronic skin condition, can be applied during surgery at the incision site, or can be applied to an open wound. The delivery device may be combined with a composition comprising a drug in unit dose form for use as a kit.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e., "lockout" feature). The device may further comprise features such as dose counting/logging or tapering methods. In addition, the device may further include a component to prevent use by unauthorized individuals, and a component to record dosing histories. These components may be used alone, or in combination with other components.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

The disclosure teaches the Staccato device as shown in FIG. 4, wherein the antistatic material is used in the airway.

Antistatic material includes but is not limited to: both airway materials which are antistatic as well as coatings for the airway. The disclosure teaches metallized airways (produced by coating the inner wall of the airway with conductive metals such as stainless steel/copper/copper/stainless steel, or by applying a metallic tape (like copper) to the inner and outer walls of the airway), the use of an antistatic spray (such as the Staticide brand) on the default airway, and the use of antistatic plastics (such as the Permastat or Permastat plus brands) as airway materials.

Typically, the drug supply article is heated to a temperature sufficient to vaporize all or a portion of the film, so that the composition forms a vapor that becomes entrained in a stream of air during inhalation. As noted above, heating of the drug supply article may be accomplished using, for example, an electrically-resistive wire embedded or inserted into the substrate and connected to a battery (28 in FIG. 4) disposed in the housing. The heating can be actuated, for example, with a button on the housing or via breath actuation, as is known in the art.

Another device that may be used to form and deliver the aerosols described herein is as follows. The device comprises an element for heating a composition to form a vapor, an element allowing the vapor to cool, thereby forming a condensation aerosol, and an element permitting a user to inhale the aerosol. The device also comprises an upper external housing member and a lower external housing member that fit together.

The downstream end of each housing member is gently tapered for insertion into a user's mouth. The upstream end of the upper and lower housing members are slotted (either one or both are slotted), to provide for air intake when a user inhales. The upper and lower housing members when fitted together define a chamber. Positioned within chamber is a drug supply unit.

The solid support may be of any desirable configuration. At least a portion of the surface of the substrate is coated with a composition film. With the case of the thermite-type heating source, the interior region of the substrate contains a substance suitable to generate heat. The substance can be a solid chemical fuel, chemical reagents that mix exothermically, electrically resistive wire, etc. A power supply source, if needed for heating, and any necessary valving for the inhalation device may be contained in end piece. A power supply source may be a piece that mates with the drug supply unit.

In one variation of the devices used, the device includes a drug composition delivery article composed of the substrate, a film of the selected drug composition on the substrate surface, and a heat source for supplying heat to the substrate at a rate effective to heat the substrate to a temperature greater than 200° C. or in other embodiments to a temperature greater than 250° C., 300° C. or 350° C., and to produce substantially complete volatilization of the drug composition within a period of 2 seconds or less.

Other drug supply articles that may be used in combination with the devices described herein. Various methods of coatings are known in the art and/or have been described above.

FIG. 4 is a schematic representation of a drug delivery device 40. The drug delivery device 40 comprises a housing 42 surrounding a drug supply unit 10 and the housing 42 defines an airway 44. In use, air can be drawn through the housing 42 via the airway 44 by drawing air in through the inlet 46 in the direction of the arrow 48 to the outlet 50. In use, a drug layer 38 is vaporized and the vaporized drug is entrained in the air and then condenses to form an aerosol in the condensation space 52 so that a condensation aerosol can be delivered through the outlet 50. The drug delivery device can be configured and dimensioned to provide required airflow rates for forming aerosol particles of select size from various drugs.

The airway housing material can be made of antistatic materials. A number of possible embodiments of the disclosure include both airway materials which are antistatic as well as coatings for the airway. The disclosure teaches metallized airways (produced by coating the inner wall of the airway with conductive metals such as stainless steel/copper/copper/stainless steel, or by applying a metallic tape (like copper) to the inner and outer walls of the airway), the use of an antistatic spray (such as the Staticide brand) on the default airway, and the use of antistatic plastics (such as the Permastat or Permastat plus brands) as airway materials.

The illustrative heating element shown as an electrical resistive wire that produces heat when a current flows through it, but as noted above, a number of different heating methods and corresponding devices are acceptable. For example, acceptable heat sources can supply heat to the drug supply article at rates that rapidly achieve a temperature sufficient to completely vaporize the composition from the support surface. For example, heat sources that achieve a temperature of 200° C. to 500° C. or more within a period of 2 seconds are typical, although it should be appreciated that the temperature chosen will be dependent upon the vaporization properties of the composition, but is typically heated to a temperature of at least about 200° C., preferably of at least about 250° C., more preferably at least about 300° C. or 350° C. Heating the substrate produces a drug composition vapor that in the presence of the flowing gas generates aerosol particles in the desired size range. The presence of the gas flow is generally prior to, simultaneous with, or subsequent to heating the substrate. In one embodiment, the substrate is heated for a period of less than about 1 second, and more preferably for less than about 500 milliseconds, still more preferably for less than about 200 milliseconds. The drug-aerosol particles are inhaled by a subject for delivery to the lung.

The device may also include a gas-flow control valve disposed upstream of the solid support, for limiting gas-flow rate through the condensation region. The gas-flow valve may, for example, include an inlet port communicating with the chamber, and a deformable flap adapted to divert or restrict airflow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit airflow rate into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

The gas control valve could, for example, function to limit air drawn into the device to a preselected level, e.g., 15 L/minute. In this way, airflow for producing particles of a desired size may be preselected and produced. For example, once this selected airflow level is reached, additional air drawn into the device would create a pressure drop across the bypass valve, which in turn would accommodate airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced. Typically, the faster the airflow, the smaller the particles are. Thus, to achieve smaller or larger particles, the gas velocity through the condensation region of the chamber may be altered by modifying the gas-flow control valve to increase or decrease the volumetric airflow rate. For example, to produce condensation particles in the size range of about 1-3.5 μm MMAD, a chamber having substantially smooth-surfaced walls would have a selected gas-flow rate in the range of 1-10 L/minute.

Additionally, as will be appreciated by one of skill in the art, particle size may be altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface.

Drug Composition Film Thickness

Typically, the drug composition film coated on the solid support has a thickness of between about 0.05-30 μm, and typically a thickness between 0.1-30 μm. More typically, the thickness is between about 0.2-30 μm; even more typically, the thickness is between about 0.5-30 μm, and most typically, the thickness is between about 0.5-25 μm. The desirable film thickness for any given drug composition is typically determined by an iterative process in which the desired yield and purity of the condensation aerosol composition are selected or known.

For example, if the purity of the particles is less than that which is desired, or if the percent yield is less than that which is desired, the thickness of the drug film is adjusted to a thickness different from the initial film thickness. The purity and yield are then determined at the adjusted film thickness, and this process is repeated until the desired purity and yield are achieved. After selection of an appropriate film thickness, the area of substrate required to provide a therapeutically effective dose is determined.

Generally, the film thickness for a given drug composition is such that drug-aerosol particles, formed by vaporizing the drug composition by heating the substrate and entraining the vapor in a gas stream, have (i) 10% by weight or less drug-degradation product, more preferably 5% by weight or less, most preferably 2.5% by weight or less and (ii) at least 50% of the total amount of drug composition contained in the film. The area of the substrate on which the drug composition film is formed is selected to achieve an effective human therapeutic dose of the drug aerosol as is described further below.

To determine the thickness of the drug film, one method that can be used is to determine the area of the substrate and calculate drug film thickness using the following relationship:

$$\text{film thickness (cm)} = \text{drug mass (g)} / [\text{drug density (g/cm}^3) \times \text{substrate area (cm}^2)]$$

The drug mass can be determined by weighing the substrate before and after formation of the drug film or by extracting the drug and measuring the amount analytically. Drug density can be experimentally determined by a variety of techniques, known by those of skill in the art or found in the literature or in reference texts, such as in the CRC. An assumption of unit density is acceptable if an actual drug density is not known.

The substrate having a drug film of known thickness was heated to a temperature sufficient to generate a thermal vapor. All or a portion of the thermal vapor was recovered and analyzed for presence of drug-degradation products, to determine purity of the aerosol particles in the thermal vapor. There is a clear relationship between film thickness and aerosol particle purity, whereas the film thickness decreases, the purity increases.

In addition to selection of a drug film thickness that provides aerosol particles containing 10% or less drug-degradation product (i.e., an aerosol particle purity of 90% or more), the film thickness is selected such that at least about 50% of the total amount of drug composition contained in the film is vaporized when the substrate is heated to a temperature sufficient to vaporize the film.

To obtain higher purity aerosols one can coat a lesser amount of drug, yielding a thinner film to heat, or alternatively use the same amount of drug but a larger surface area. Generally, except for, as discussed above, extremely thin thickness of drug film, a linear decrease in film thickness is associated with a linear decrease in impurities.

Thus for the drug composition where the aerosol exhibits an increasing level of drug degradation products with increasing film thicknesses, particularly at a thickness of greater than 0.05-30 microns, the film thickness on the substrate will typically be between 0.05 and 30 microns, e.g., the maximum or near-maximum thickness within this range that allows formation of a particle aerosol with drug degradation less than 5%.

Another approach contemplates generation of drug-aerosol particles having a desired level of drug composition purity by forming the thermal vapor under a controlled atmosphere of an inert gas, such as argon, nitrogen, helium, and the like.

Once a desired purity and yield have been achieved or can be estimated from a graph of aerosol purity versus film thickness and the corresponding film thickness determined, the area of substrate required to provide a therapeutically effective dose is determined.

Substrate Area

As noted above, the surface area of the substrate surface area is selected such that it is sufficient to yield a therapeutically effective dose. The amount of drug to provide a therapeutic dose is generally known in the art and is discussed more below. The required dosage and selected film thickness, discussed above, dictate the minimum required substrate area in accord with the following relationship:

$$\text{film thickness (cm)} \times \text{drug density (g/cm}^3) \times \text{substrate area (cm}^2) = \text{dose (g)}$$

OR $$\text{Substrate area (cm}^2) = \text{dose (g)} / [\text{film thickness (cm)} \times \text{drug density (g/cm}^3)]$$

The drug mass can be determined by weighing the substrate before and after formation of the drug film or by extracting the drug and measuring the amount analytically. Drug density can be determined experimentally by a variety of well-known techniques, or may be found in the literature or in reference texts, such as in the CRC. An assumption of unit density is acceptable if an actual drug density is not known.

To prepare a drug supply article comprised of a drug film on a heat-conductive substrate that is capable of administering an effective human therapeutic dose, the minimum substrate surface area is determined using the relationships described above to determine a substrate area for a selected film thickness that will yield a therapeutic dose of drug aerosol.

In some variations, the selected substrate surface area is between about 0.05-500 cm$^2$. In others, the surface area is between about 0.05 and 300 cm$^2$. In one embodiment, the substrate surface area is between 0.05 and 0.5 cm$^2$. In one embodiment, substrate surface areas, are between 0.1 and 0.2 cm$^2$. The actual dose of drug delivered, i.e., the percent yield or percent emitted, from the drug-supply article will depend on, along with other factors, the percent of drug film that is vaporized upon heating the substrate. Thus, for drug films that yield upon heating 100% of the drug film and aerosol particles that have a 100% drug purity, the relationship between dose, thickness, and area given above correlates directly to the dose provided to the user. As the percent yield and/or particle purity decrease, adjustments in the substrate area can be made as needed to provide the desired dose. Also, as one of skill in the art will recognize, larger substrate areas other than the minimum calculated area for a particular film thickness can be used to deliver a therapeutically effective dose of the drug. Moreover as can be appreciated by one of skill in art, the film need not coat the complete surface area if a selected surface area exceeds the minimum required for delivering a therapeutic dose from a selected film thickness.

Dosage of Drug Containing Aerosols

The dose of a drug delivered in the aerosol refers to a unit dose amount that is generated by heating of the drug under defined conditions, cooling the ensuing vapor, and delivering the resultant aerosol. A "unit dose amount" is the total amount of drug in a given volume of inhaled aerosol. The unit dose amount may be determined by collecting the aerosol and analyzing its composition as described herein, and comparing the results of analysis of the aerosol to those of a series of reference standards containing known amounts of the drug. The amount of drug or drugs required in the starting composition for delivery as an aerosol depends on the amount of drug or drugs entering the thermal vapor phase when heated (i.e., the dose produced by the starting drug or drugs), the bioavailability of the aerosol drug or drugs, the volume of patient inhalation, and the potency of the aerosol drug or drugs as a function of plasma drug concentration.

One can determine the appropriate dose of a drug-containing aerosol to treat a particular condition using methods such as animal experiments and a dose-finding (Phase I/II) clinical trial. These experiments may also be used to evaluate possible pulmonary toxicity of the aerosol. One animal experiment involves measuring plasma concentrations of drug in an animal after its exposure to the aerosol. Mammals such as dogs or primates are typically used in such studies, since their respiratory systems are similar to that of a human and they typically provide accurate extrapolation of test results to humans. Initial dose levels for testing in humans are generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered. The actual effective amount of drug for a particular patient can vary according to the specific drug or combination thereof being utilized, the particular composition formulated, the mode of administration and the age, weight, and condition of the patient and severity of the episode being treated.

Particle Size

Efficient aerosol delivery to the lungs requires that the particles have certain penetration and settling or diffusional characteristics. Deposition in the deep lungs occurs by gravitational settling and requires particles to have an effective settling size, defined as mass median aerodynamic diameter (MMAD), typically between 1-3.5 µm. For smaller particles, deposition to the deep lung occurs by a diffusional process that requires having a particle size in the 10-100 nm, typically 20-100 nm range. An inhalation drug-delivery device for deep lung delivery should produce an aerosol having particles in one of these two size ranges, preferably between about 0.1-3 m MMAD. Typically, in order to produce particles having a desired MMAD, gas or air is passed over the solid support at a certain flow rate.

During the condensation stage the MMAD of the aerosol is increasing over time. Typically, in variations of the invention, the MMAD increases within the size range of 0.01-3 microns as the vapor condenses as it cools by contact with the carrier gas then further increases as the aerosol particles collide with each other and coagulate into larger particles. Most typically, the MMAD grows from <0.5 micron to >1 micron in less than 1 second. Thus typically, immediately after condensing into particles, the condensation aerosol MMAD doubles at least once per second, often at least 2, 4, 8, or 20 times per second. In other variations, the MMAD increases within the size range of 0.1-3 microns.

Typically, the higher the flow rate, the smaller the particles that are formed. Therefore, in order to achieve smaller or larger particles, the flow rate through the condensation region of the delivery device may be altered. A desired particle size is achieved by mixing a compound in its vapor-state into a volume of a carrier gas, in a ratio such that the desired particle size is achieved when the number concentration of the mixture reaches approximately $10^9$ particles/mL. The particle growth at this number concentration is then slow enough to consider the particle size to be "stable" in the context of a single deep inhalation. This may be done, for example, by modifying a gas-flow control valve to increase or decrease the volumetric airflow rate. To illustrate, condensation particles in the size range 0.1-3 µm MMAD may be produced by selecting the gas-flow rate over the vaporizing drug to be in a range of 1-10 L/minute, preferably in the range of 2-8 L/min.

Additionally, as will be appreciated by one of skill in the art, particle size may also be altered by modifying the cross-section of the chamber condensation region to increase or decrease linear gas velocity for a given volumetric flow rate. In addition, particle size may also be altered by the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface.

Analysis of Drug Containing Aerosols

Purity of a drug-containing aerosol may be determined using a number of different methods. It should be noted that when the term "purity" is used, it refers to the percentage of aerosol minus the percent byproduct produced in its formation. Byproducts for example, are those unwanted products produced during vaporization. For example, byproducts include thermal degradation products as well as any unwanted metabolites of the active compound or compounds. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of byproduct. Any suitable trap may be used. Suitable traps include filters, glass wool, impingers, solvent traps, cold traps, and the like. Filters are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard(s), an approach well known in the art.

In many cases, the structure of a byproduct may not be known or a standard for it may not be available. In such cases, one may calculate the weight fraction of the byproduct by assuming it has an identical response coefficient (e.g. for ultraviolet absorption detection, identical extinction coefficient) to the drug component or components in the drug composition. When conducting such analysis, byproducts present in less than a very small fraction of the drug compound, e.g. less than 0.1% or 0.03% of the drug compound, are typically excluded. Because of the frequent necessity to assume an identical response coefficient between drug and byproduct in calculating a weight percentage of byproduct, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis. In certain cases where analysis of the drug by UV are not viable, other analytical tools such as GC/MS or LC/MS may be used to determine purity.

It is possible that changing the gas under which vaporization of the composition occurs may also impact the purity.

Other Analytical Methods

Particle size distribution of a drug-containing aerosol may be determined using any suitable method in the art (e.g., cascade impaction). A Next Generation Cascade Impactor (MSP Corporation, Shoreview, Minn.) linked to a vaporization device by an induction port (USP induction port, MSP Corporation, Shoreview, Minn.) is one system used for cascade impaction studies.

Inhalable aerosol mass density may be determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2-4 liters.

Inhalable aerosol drug mass density may be determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2-4 liters. The amount of active drug compound collected in the chamber is determined by extracting the chamber, conducting chromatographic analysis of the extract and comparing the results of the chromatographic analysis to those of a standard containing known amounts of drug.

Inhalable aerosol particle concentration may be determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$7*D^3*\varphi/6$, where D is a typical particle diameter in the size range (generally, the mean boundary MMADs defining the size range) in microns, $\varphi$ is the particle density (in g/mL) and mass is given in units of picograms ($g^{-12}$).

Rate of inhalable aerosol particle formation may be determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 10 nm to 5 micron particles collected divided by the duration of the collection time.

Rate of aerosol formation may be determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation may be determined, for example, by delivering a drug-containing aerosol into a confined chamber via an inhalation device over a set period of time (e.g., 3 s). Where the aerosol is a pure drug, the amount of drug collected in the chamber is measured as described above. The rate of drug aerosol formation is equal to the amount of drug collected in the chamber divided by the duration of the collection time. Where the drug-containing aerosol comprises a pharmaceutically acceptable excipient, multiplying the rate of aerosol formation by the percentage of drug in the aerosol provides the rate of drug aerosol formation.

Kits

In an embodiment of the invention, a kit is provided for use by a healthcare provider, or more preferably a patient. The kit for delivering a condensation aerosol typically comprises a composition comprising a drug, and a device for forming a condensation aerosol. The composition is typically void of solvents and excipients and generally comprises a heat stable drug. The device for forming a condensation aerosol typically comprises an element configured to heat the composition to form a vapor, an element allowing the vapor to condense to form a condensation aerosol, and an element permitting a user to inhale the condensation aerosol. The device in the kit may further comprise features such as breath-actuation or lockout elements or dose counting/logging or tapering devices. An exemplary kit will provide a hand-held aerosol delivery device and at least one dose.

In another embodiment, kits for delivering a drug aerosol comprising a thin film of the drug composition and a device for dispensing said film as a condensation aerosol are provided. The composition may contain pharmaceutical excipients. The device for dispensing said film of a drug composition as an aerosol comprises an element configured to heat the film to form a vapor, and an element allowing the vapor to condense to form a condensation aerosol.

In the kits of the invention, the composition is typically coated as a thin film, generally at a thickness between about 0.5-30 microns, on a substrate which is heated by a heat source. Heat sources typically supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. To prevent drug degradation, it is preferable that the heat source does not heat the substrate to temperature greater than 600° C. while the drug film is on the substrate to prevent. More preferably, the heat source does not heat the substrate in to temperatures in excess of 500° C.

The kit of the invention can be comprised of various combinations of drug and drug delivery devices. In some embodiments the device may also be present with more than one drug. The other drug may be administered orally or topically. Generally, instructions for use are included in the kits.

The term "drug" as used herein means any chemical compound that is used in the prevention, diagnosis, treatment, or cure of disease, for the relief of pain, or to control or improve any physiological or pathological disorder in humans or animals. Any suitable drug compound may be used. Drugs that can be used include, for example but not limitation, drugs of one of the following classes: anesthetics, anticonvulsants, antidepressants, antidiabetic agents, antidotes, antiemetics, antihistamines, anti-infective agents, antineoplastics, antiparkisonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

Typically, where the drug is an anesthetic, it is selected from one of the following compounds: ketamine and lidocaine.

Typically, where the drug is an anticonvulsant, it is selected from one of the following classes: GABA analogs, tiagabine, vigabatrin; barbiturates such as pentobarbital; benzodiazepines such as alprazolam, clonazepam; hydantoins such as phenytoin; phenyltriazines such as lamotrigine; miscellaneous anticonvulsants such as carbamazepine, topiramate, valproic acid, and zonisamide.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranyleypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

Typically, where the drug is an antidiabetic agent, it is selected from one of the following compounds: pioglitazone, rosiglitazone, and troglitazone.

Typically, where the drug is an antidote, it is selected from one of the following compounds: edrophonium chloride, flumazenil, deferoxamine, nalmefene, naloxone, and naltrexone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

Typically, where the drug is an antihistamine, it is selected from one of the following compounds: astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

Typically, where the drug is an anti-infective agent, it is selected from one of the following classes: antivirals such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefmetazole, cefazolin, cephalexin, cefoperazone, cefoxitin, cephacetrile, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

Typically, where the drug is an anti-neoplastic agent, it is selected from one of the following compounds: droloxifene, tamoxifen, and toremifene.

Typically, where the drug is an antiparkisonian drug, it is selected from one of the following compounds: rotigotine, amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Typically, where the drug is an antirheumatic agent, it is selected from one of the following compounds: diclofenac, hydroxychloroquine and methotrexate.

Typically, where the drug is an antipsychotic, it is selected from one of the following compounds: acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine, and zuclopenthixol.

Typically, where the drug is an anxiolytic, it is selected from one of the following compounds: alprazolam, bromazepam, diazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Typically, where the drug is an appetite stimulant, it is dronabinol.

Typically, where the drug is an appetite suppressant, it is selected from one of the following compounds: fenfluramine, phentermine and sibutramine.

Typically, where the drug is a blood modifier, it is selected from one of the following compounds: cilostazol and dipyridamol.

Typically, where the drug is a cardiovascular agent, it is selected from one of the following compounds: benazepril, captopril, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocainide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazem, nifedipine, verapamil, spironolactone, bumetanide, ethacrynic acid, furosemide, torsemide, amiloride, triamterene, and metolazone.

Typically, where the drug is a central nervous system stimulant, it is selected from one of the following compounds: amphetamine, brucine, caffeine, dexfenfluramine, dextroamphetamine, ephedrine, fenfluramine, mazindol, methylphenidate, pemoline, phentermine, sibutramine, and modafinil.

Typically, where the drug is a drug for Alzheimer's disease management, it is selected from one of the following compounds: donepezil, galanthamine and tacrin.

Typically, where the drug is a drug for cystic fibrosis management, it is selected from one of the following compounds: CPX, IBMX, XAC and analogues; 4-phenylbutyric acid; genistein and analogous isoflavones; and milrinone.

Typically, where the drug is a diagnostic agent, it is selected from one of the following compounds: adenosine and aminohippuric acid.

Typically, where the drug is a dietary supplement, it is selected from one of the following compounds: melatonin and vitamin-E.

Typically, where the drug is a drug for erectile dysfunction, it is selected from one of the following compounds: tadalafil, sildenafil, vardenafil, apomorphine, apomorphine diacetate, phentolamine, and yohimbine.

Typically, where the drug is a gastrointestinal agent, it is selected from one of the following compounds: loperamide, atropine, hyoscyamine, famotidine, lansoprazole, omeprazole, and rebeprazole.

Typically, where the drug is a hormone, it is selected from one of the following compounds: testosterone, estradiol, and cortisone.

Typically, where the drug is a drug for the treatment of alcoholism, it is selected from one of the following compounds: naloxone, naltrexone, and disulfiram.

Typically, where the drug is a drug for the treatment of addiction it is buprenorphine.

Typically, where the drug is an immunosupressive, it is selected from one of the following compounds: mycophenolic acid, cyclosporin, azathioprine, tacrolimus, and rapamycin.

Typically, where the drug is a mast cell stabilizer, it is selected from one of the following compounds: cromolyn, pemirolast, and nedocromil.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a motion sickness product, it is selected from one of the following compounds: diphenhydramine, promethazine, and scopolamine.

Typically, where the drug is a drug for multiple sclerosis management, it is selected from one of the following compounds: bencyclane, methylprednisolone, mitoxantrone, and prednisolone.

Typically, where the drug is a muscle relaxant, it is selected from one of the following compounds: baclofen, chlorzoxazone, cyclobenzaprine, methocarbamol, orphenadrine, quinine, and tizanidine.

Typically, where the drug is a nonsteroidal anti-inflammatory, it is selected from one of the following compounds: aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Typically, where the drug is another analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is an opthalmic preparation, it is selected from one of the following compounds: ketotifen and betaxolol.

Typically, where the drug is an osteoporosis preparation, it is selected from one of the following compounds: alendronate, estradiol, estropitate, risedronate and raloxifene.

Typically, where the drug is a prostaglandin, it is selected from one of the following compounds: epoprostanol, dinoprostone, misoprostol, and alprostadil.

Typically, where the drug is a respiratory agent, it is selected from one of the following compounds: albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, and pirfenidone Typically, where the drug is a sedative and hypnotic, it is selected from one of the following compounds: butalbital, chlordiazepoxide, diazepam, estazolam, flunitrazepam, flurazepam, lorazepam, midazolam, temazepam, triazolam, zaleplon, zolpidem, and zopiclone.

Typically, where the drug is a skin and mucous membrane agent, it is selected from one of the following compounds: isotretinoin, bergapten and methoxsalen.

Typically, where the drug is a smoking cessation aid, it is selected from one of the following compounds: nicotine, nicotine meta-salicylate and varenicline.

Typically, where the drug is a Tourette's syndrome agent, it is pimozide.

Typically, where the drug is a urinary tract agent, it is selected from one of the following compounds: tolteridine, darifenicin, propantheline bromide, and oxybutynin.

Typically, where the drug is a vertigo agent, it is selected from one of the following compounds: betahistine and meclizine.

In general, we have found that suitable drug have properties that make them acceptable candidates for use with the devices and methods herein described. For example, the drug compound is typically one that is, or can be made to be, vaporizable. Typically, the drug is a heat stable drug. Exemplary drugs include acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenytoin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocainide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, and triamcinolone acetonide and pharmaceutically acceptable analogs and equivalents thereof.

It is noted that the above listings of drugs into categories does not limit the use of a drug in one category with regard to an alternate use in another category, or a new category.

Pharmaceutically acceptable excipients may be volatile or nonvolatile. Volatile excipients, when heated, are concurrently volatilized, aerosolized and inhaled with the drug intended to be delivered. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; and mixtures thereof.

The disclosure teaches the use of antistatic materials in the airway for thermal aerosol generation devices regarding drugs susceptible to charging during aerosol generation. These may include but are not limited to, the above listed drugs.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

Example 1: Electrostatic Phenomena in Thermal Condensation Aerosols

Here, we present an electrical characterization of thermal condensation aerosols of a number of drugs on the Staccato® system.

Methods

Test Formulation and Device

Several benzodiazepine drugs (alprazolam, estazolam, triazolam, diazepam, clobazam), loxapine, prochloiperazine, and zaleplon were used on the Staccato single dose platform. The Staccato single dose platform is breath-actuated and consists of a thin film of excipient-free drug coated on a stainless steel substrate inside a plastic airway housing. As a patient inhales through the device, the substrate becomes hot from an internal energy source. The drug film rapidly vaporizes and is entrained into the air stream inside the airway housing, ultimately condensing into an aerosol (FIG. 1), Vapor-phase drug cools nearly instantaneously in air stream, causing condensation of the drug into 1-3 μm aerosol particles. See FIG. 1.

Drug formulation: Alprazolam, estazolam, triazolam, diazepam, clobazam, loxapine, prochlorperazine, and zaleplon Free base form of drug dissolved in appropriate solvent, spray coated onto substrate at film thickness of 3-8 μm.

Electrometer: TSI Model 3068A Aerosol Electrometer Measures total net charge on aerosol drug particles.

ESD Simulator: Schaffner model NSG 435 ESD simulator; Induces specific polarization and quantity of electrical potential to the plastic airway housing.

Procedure: Experiment 1a: Net Charge Measurement

Total net charge of aerosol particles was measured using an aerosol electrometer (TS13068A). The sample inlet flow rate was set at 1.0 LPM as it was the upper limit of the aerosol.

Electrometer. The device was manually triggered, resulting in device actuation, heating and vaporization of the drug film, and the subsequent condensation of the drug into aerosol particles. The electrometer was connected to an oscilloscope to capture current output of the aerosol. The total net charge of the aerosol was calculated by integrating the current vs. time curve from the oscilloscope and dividing by the total drug mass emitted from the device. At least two equivalent trials were run for each drug.

Experiment 1b: Effect of Induction Charging on Airway Housing Deposition

Aerosol deposition onto the airway housing was determined by connecting a filter holder (Pall in-line filter holder) containing a glass fiber filter (Whatman) to a vacuum pump. Airflow rate was set at 15 LPM for a duration of 5 seconds. Once the setup was completed, a potential of either +16 kV or −16 kV was applied to the plastic airway housing using the ESD simulator. The airflow was initiated by switching on a solenoid valve, resulting in device actuation. After device actuation, the Staccato device was opened and the airway housings were assayed through extraction and high performance liquid chromatography analysis to determine aerosol deposition. At least three equivalent trials were run for each drug unless noted otherwise.

Experiment 2: Total Net Charge Vs. Airway Housing Deposition: Total Net Charge (Part 1a) and Housing Deposition were Measured Simultaneously for Staccato Alprazolam. Two Staccato Alprazolam device versions were tested in this part of the study. The first version (used in Part 1) used an airway housing made of polycarbonate with a surface resistivity of—1×10 18 0/sq. The second version used an airway housing made of a lower resistivity polycarbonate (−1×1011 0/sq) to provide charge dissipation.

Results and Discussion

Most thermal condensation drug aerosols did not show high electrical charge content. However, the total net charges of aerosol particles for certain structurally-similar benzodiazepines (alprazolam, estazolam and triazolam) were substantial (Table 1).

Induction charging on the housing by means of an applied voltage field amplifies the effects of electrostatic interactions and aerosol deposition on the housing components. Aerosol deposition on the airway housing results for alprazolam, prochlorperazine, and loxapine are shown in Table L. Overall, induction charging on the housing showed minimal effect for prochlorperazine or loxapine aerosols. Although not tested with an applied field, zaleplon also showed negligible airway housing deposition. For alprazolam aerosols, airway housing deposition increased significantly when the housing was charged positively, which suggests that the alprazolam aerosol is negatively charged. This observation is consistent with the net charge result for alprazolam aerosol from Part 1a. The charging process likely occurs from a triboelectric separation of dissimilar materials (an organic drug and a steel substrate). Why it occurs for certain benrzodiazepines like alprazolam, estazolam, and triazolam and not for the other drugs is not known for certain, but is likely a function of the molecular structure of alprazolam, estazolam and triazolam and their stability in delocalizing an additional free electron.

TABLE 1

Net charge and aerosol deposition on housing (values are means ± SD).

| Drug | Net Charge Measurement Net Charge (pC/mg) | Applied Potential to Airway Housing | Aerosol Deposition on Housing (% Loaded Dose) |
|---|---|---|---|
| Alprazolam | Not measured | +16 kV | 45 ± 6 |
|  |  | −16 kV | 12 ± 4 |
|  | −252 ± 59 | None | 12 ± 6 |
| Estazolam | −202 ± 3 | None | Not measured |
| Triazolam | −158 ± 13 | None |  |
| Diazepam | −1 ± 1 | None |  |
| Clobazam | 0 ± 0 | None |  |
| Loxapine | Not measured | +16 kV | 01 |
|  |  | −16 kV | 11 |
|  |  | None | 2 ± 2 |
| Prochlorperazine | Not measured | +16 kV | 71 |
|  |  | −16 kV | 31 |
|  | 27 ± 3 | None | 3 ± 3 |
| Zaleplon | 7 ± 1 | None | 0 ± 0 |

Previous work shows conductive surfactant coatings on device component surfaces are effective in dissipating charges [9-10]. Here, an anti-static polycarbonates with significantly lower electrical resistivity than the standard polycarbonate was used for Staccato Alprazolam in an attempt to reduce airway housing deposition and losses in emitted dose. Total net charge of alprazolam particles as well as airway housing deposition were measured for standard Staccato Alprazolam and Staccato Alprazolam devices with anti-static housing material. Results are shown in Table 2. Total net charge on alprazolam particles emitted nom the anti-static housing is 100-fold less than that nom the standard housing while aerosol deposition OD the airway housing was likewise reduced significantly in the anti-static housing.

TABLE 2

Total net charge and aerosol deposition on the airway housing for standard polycarbon Vs. anti-static polycarbonate materials (values are means ± SD, N-4).

| Airway housing material | Net charge | Aerosol deposition on airway housing (% Loaded Dose) |
|---|---|---|
| Standard polycarbonate | −279 ± 45 | 15 ± 2 |
| Anti-static polycarbonate | −2.2 ± 1 | 0 ± 0 |

Electrostatic phenomena in thermal condensation aerosols of several benzodiazepines (alprazolam, estazolam, triazolan, diazepam, clobazam), prochlorperazine, loxapine, and zaleplon were investigated. Alprazolam aerosols showed a relatively large net negative charge, which can lead to substantially higher aerosol deposition on the airway housing. To overcome the electrostatic interactions, a more conductive polycarbonate was used for the housing. This significantly reduced the total net charge of the alprazolam aerosol as well as the airway housing deposition.

Example 2

Aerosol charge testing with heat packages and screening foils using the aerosol electrometer. For screening foils, aerosol charge had small magnitude and positive polarity and no trend with coating density. For Staccato heat packages, aerosol charge was large and negative without Staticide, while with Staticide it was small and negative. Bumetanide and PCZ aerosols had negatively charged aerosols about one order of magnitude lower than Alprazolam.

Example 3

Aerosol charge testing using heat packages and funnels as entry ways into the aerosol electrometer. Heat packages were actuated without housings. With a galvanized steel funnel, a negative polarity charge was generated. With a plastic funnel, a positive polarity charge was generated. Additional tests showed that a partially Staticide-coated airway generated positive polarity Alprazolam aerosol. Other tests showed that Zaleplon devices had a low degree of charge.

Example 4

Aerosol charge testing using Permastat and Permastat plus airways. Airways made with Permastat and Permastat plus conductive polycarbonate alloys showed a very significant reduction in aerosol charging and airway deposition when compared with the standard airway material.

Example 5

Aerosol charge testing using screening foil apparatus modified to apply a static electric field to the screening foil during vaporization. This experiment showed that the degree of aerosol charging increased monotonically with strength of applied potential differences. However, the potential difference used (0V to 5 kV) led to saturation of the electrometer's sensor.

Example 6

Follow-up aerosol charge testing using screening foil apparatus modified to apply a static electric field to the screening foil during vaporization. Due to saturation at higher voltages, the applied voltage range in this experiment set was 0V to 500V. Again, a monotonic trend in increased aerosol charge with increased electric field strength was observed.

Example 7

Aerosol charge testing using metallized housing to apply a static electric field to the heat package during vaporization. Phase 2A2 DCT2 aerosol properties testing (PSD, ED, and EP with 0.5 mg ALP) at 28.3 LPM. This DCT led to the static study for ALP. Higher airway deposition was found from devices tested 4 days after drug coating (crystallized) instead of testing on the same day (amorphous). Drug crystals were found on both HP and airway after actuating devices that were coated for 4 days (first time seeing these).

Example 8

Types of HP (1 vs. 2 sided) and coating spray rate study. Phase 2A2 DCT2 ED & EP at 28.3 LPM (1.5 mg). Original coating parameters were tested on both 1 and 2-sided HP and drug crystals were found on the airway with both kind of HP. Lower spray rate was applied but drug crystals were still found on airways. Presence of drug crystals on the airway was not caused by 1 or 2-sided HP or lower spray rate.

Example 9

Coating spray rate. Phase 2A2 DCT2 ED at 28.3 LPM (0.5 mg) with lower spray rate. Ave airway deposition was 10%. Drug crystals were present in all airways after actuation. Again, lower spray rate did not solve the airway deposition problem.

Example 10

Hot vs. cold HP with lower spray rate. Phase 2A2 DCT2, ED & EP at 28.3 LPM, 1.5 mg. Cold HP had less drug crystals on the airway, both visually and quantitatively.

Example 11

Airway deposition check using HP from Lot M0167, PNF0027, 1 mg. Low airway deposition (no crystals) when devices were held no gloves, but high (with drug crystals) when held with gloves.

Example 12

Airway deposition check on the effect of 1) holding HPs with and without gloves using HP with 1 and 2 passes coating and, 2) with the use of ESD gun (8 kV+, 8 kV−, 16 kV+). Airway deposition was higher when gloves were used and higher as the ESD gun increased its positive polarity (highest with 16 kV+, lowest with 8 kV−). This also suggested that ALP aerosols are net negatively charged.

Example 13

Effect of 16 kV+, 16 kV−, and ground conditions on clamshell and front/back airways deposition. Results showed that clamshell airways with 16 kV+ had the highest airway deposition, followed by grounded airways, and the least when 16 kV− was applied. Similar trend was found with front/back airways but with a smaller amount of deposition.

Example 14

Effect of 16 kV+ and 16 kV− on PCZ and Loxapine. Results showed that there was no major effect on airway deposition from +/−16 kV.
Effect of gloves on PCZ and Loxapine airway deposition and effect of +/−16 kV and grounded conditions on ALP airway deposition. Gloves did not have any effect on airway deposition with PCZ and Loxapine. 16 kV+ still gave the highest airway deposition with ALP, 16 kV− and grounded condition had about the same amount of ALP airway deposition but less than 16 kV+. This study also showed that large amount of ALP airway deposition was found with amorphous coating.

Example 15

Comparison of ALP airway deposition with grounded and ungrounded conditions at high and low humidity environment. This study showed that airway deposition was a lot higher at low humidity (20% RH) as compared to 40% RH. However, the study did not show any significant differences between grounded and ungrounded conditions under both humidity settings.

Comparison of ALP airway deposition at 2 different humidity conditions (28 & 55% RH) with and without grounding the person and the measurement of charge using an electrometer at various stages from the device being inside the foil pouch to the moment during actuation. Results showed that airway deposition at 28% RH were in general higher than at 55% RH. By grounding the person holding the device, airway deposition decreased in most cases. The electrometer study showed that 1) some static charge was already present on the foil pouch, 2) static charge on the airways increased after pull tab was removed in most cases, and 3) ground the person during actuation lowered static charge on the airways.

Example 16

ALP airway deposition study with the use of anti-static spray and copper tape. This study showed that both anti-static spray and copper tape can reduce airway deposition even with 16 kV+ applied onto the airways.

ALP airway deposition study with the use of anti-static spray and copper tape at low humidity (27% RH). This study showed that anti-static spray and copper tape can help reduce airway deposition even at low humidity condition.

ALP airway deposition study with the use of anti-static spray where HP had normal reactant propagation time (previous studies, A152p144-151 used HP with slower propagation time). Results once again showed that anti-static spray reduce airway deposition, independent of reactant propagation time.

Example 17

ALP airway deposition study where external actuation (with actuation box) and pull tab actuation were compared when the airway was 1) applied with 16 kV+, 2) held without gloves, 3) grounded. Results showed there was no difference in airway deposition between pull tab and external actuation under the 3 conditions studied. Deposition was not reduced.

Example 18

ALP airway deposition study where 1) airways were pre-washed with IPA prior to testing, 2) airways were built without check valve. Results showed that both cases did not reduce airway deposition.

Example 19

ALP airway deposition study where devices were built by manufacturing group and tested without gloves using 1-sided HP (front/back airways) and 2-sided HPs (clamshell airways). Results showed that 1-sided HP had higher airway deposition (16%) while 2-sided HP had lower airway deposition (2%).

Example 20

ALP airway deposition study where devices were built by manufacturing group and 16 kV+ were applied onto the airways. 1-sided HP (front/back airways) and 2-sided HP (clamshell airways) were tested. Results showed that 1-sided HP (17%) had higher airway deposition than the 2-sided ones (1%).

Example 21

Comparison of ALP airway deposition between devices built by manufacturing group and R&D (Jasmine) and a list of assembly differences between the two were identified. 16 kV+ was applied onto the airways. Results showed that devices built by manufacturing had a lower airway deposition.

Example 22

Comparison of ALP airway deposition between pouched and unpouched (devices were removed from foil pouch 20 hrs before testing) devices. 16 kV+ was applied onto the airways. Results showed that there were no significant differences on airway deposition between the two conditions.

Example 24

Comparison of ALP airway deposition on the effect of +/−16 kV. These devices were built by manufacturing. Results showed that both conditions had little airway deposition.

Example 25

ALP airway deposition study where all the devices were built and pouched by manufacturing group. QC group tested both control (normal) and staticide devices without 16 kV+. R&D group tested both control (normal) and staticide devices with 16 kV+ applied onto the airways. These were tested throughout a period of 16 days. Results showed that there were more airway depositions on the control (normal) devices than the staticide ones. All the staticide devices from both QC and R&D groups had very low airway deposition. The control (normal) devices had more airway deposition when tested by R&D as compared to QC.

Example 26

ALP airway deposition study with +16 kV on manufacturing assembled devices (first batch). Very little airway deposition was found.

Example 27

ALP airway deposition study where HPs were coated with DCM ALP solution instead of methanol/acetone 50/50 ALP solution. Results showed that DCM coating solution did not help reduce airway deposition.

Example 28

ALP airway deposition study with the use of ionizer. Results showed that ionizer reduced airway deposition.

Example 29

Airway deposition study with ALP, PCZ, and Loxapine at 10 LPM. For ALP, results showed that staticide devices had low airway deposition, normal (control) devices that were built by R&D had high airway deposition, while built by manufacturing was a bit lower. PCZ had very little airway deposition, but Loxapine had lots of airway deposition.

Example 30

ALP airway deposition study where devices were pouched on different days with different humidity. Results showed that airway deposition in general did not change much but there were a few devices that had higher airway depositions.

Example 31

HP surface and aerosol charge measurement for 1) normal/control airway with ALP, 2) staticide airway with ALP, 3) normal/control airway (placebo), and 4) staticide airway (placebo). Results showed that normal airway with ALP had the highest aerosol charge while others had very low charge, all with negative polarity. HP surface charge was positive in all normal airways. In staticide airways, HP charge seemed to have a higher variability where positive, zero, and negative charges were measured. It was also found that deposition amounts on staticide airways were around 0%.

Example 32

Aerosol charge and airway deposition study using normal (control), metallized, and Permastat plus airways. For normal airway, both aerosol charge and airway deposition were high. For metallized airway, aerosol charge was mostly high but airway deposition was low. For Permastat plus airway, both aerosol charge and airway deposition were low.

Example 33

Aerosol properties test using Permastat airway at 28.3 LPM. ED, PSD, and EP are all good and within expectations. Almost zero deposition was found on the airways.

Example 34

Aerosol charge and airway deposition using Permastat airways with different surface resistance. Airway depositions were negligible in all cases. Aerosol charge was low but majority of them had positive charge instead of negative charge.

Example 35

Aerosol charge and airway deposition using Permastat airways and normal airways (a continuation of previous study A233p110-p115). This study further confirmed that airway depositions were negligible with Permastat airways and aerosol charge was low, with both positive and negative charges measured. Normal airways that were assembled by manufacturing group had lower airway deposition and lower charge (positive and negative charges) while assembled by R&D had higher airway deposition and a much higher aerosol charge (negative charge).

Example 36

Comparison of EP between normal airways bonded by acetone and Permastat airways bonded by THF. Results showed that there was no difference in EP.

Example 37

Leak test and Pull test using Permastat airways bonded by Loctite and normal (control) airways bonded by acetone. Leak rates were good for both airways. Less force was needed to pull the Permastat airways apart as compared to the normal airways.

Example 38

I. Airway Deposition and aerosol charges for Permastat, Permastat Plus, and standard airway material (#3)
  Purpose:
    To find out the aerosol charge generated from Permastat and Permastat Plus airways and to compare that to normal airway (control)
  Materials/Equipment
  Standard airway material: makrolon polycarbonate
  Permastat: surface resistivity ~1E11 ohm/sq
  Permastat Plus: surface resistivity ~1E9 ohm/sq
  Drug: alprazolam
  Experimental Setup
  A single dose Staccato Alprazolam device was placed in a mouthpiece that was attached to the aerosol electrometer
  Aerosol generated at 28.3 LPM was captured in the aerosol electrometer and was measured in terms of current (pA)
  The current measured was recorded in the computer and charge was calculated by integrating the current-time graph
  Housing was extracted with solvent and amount of drug was determined using HPLC

TABLE 3

| Device | Description | Coated dose (mg) | Emitted dose (%) | Airway deposition (%) | Mean airway deposition (%) | Stdev Airway deposition (%) | Charge/ mass (pC/mg) | Mean charge/ mass (pC/mg) | Stdev charge/ mass (pC/mg) |
|---|---|---|---|---|---|---|---|---|---|
| | | | | Testing static dissipative airways with alprazolam at 28.3 LPM | | | | | |
| 1 | AZ002 | 1 | 80.7 | 16.1 | 15.1 | 2.0 | −241.2 | −279.2 | 45.3 |
| 2 | control | 1 | 84.3 | 12.3 | | | −264.9 | | |

TABLE 3-continued

| Device | Description | Coated dose (mg) | Emitted dose (%) | Airway deposition (%) | Mean airway deposition (%) | Stdev Airway deposition (%) | Charge/ mass (pC/mg) | Mean charge/ mass (pC/mg) | Stdev charge/ mass (pC/mg) |
|---|---|---|---|---|---|---|---|---|---|
| | | | Testing static dissipative airways with alprazolam at 28.3 LPM | | | | | | |
| 3 | (normal) | 1 | 81.3 | 15.0 | | | −265.8 | | |
| 4 | | 1 | 78.8 | 16.8 | | | −344.9 | | |
| 1 | AZ002 | 1 | 96.6 | 0.2 | 0.12 | 0.04 | −52.7 | −46.2 | 60.7 |
| 2 | Permastat | 1 | 96.1 | 0.1 | | | 1.0 | | |
| 3 | | 1 | 96.2 | 0.1 | | | −129.6 | | |
| 4 | | 1 | 95.7 | 0.1 | | | −3.6 | | |
| 1 | AZ002 | 1 | 96.7 | 0.04 | 0.07 | 0.09 | −1.7 | −2.2 | 1.3 |
| 2 | Permastat | 1 | 95.9 | 0.03 | | | −1.7 | | |
| 3 | Plus | 1 | 96.3 | 0.00 | | | −4.2 | | |
| 4 | | 1 | 96.1 | 0.20 | | | −1.3 | | |

Figure 2:
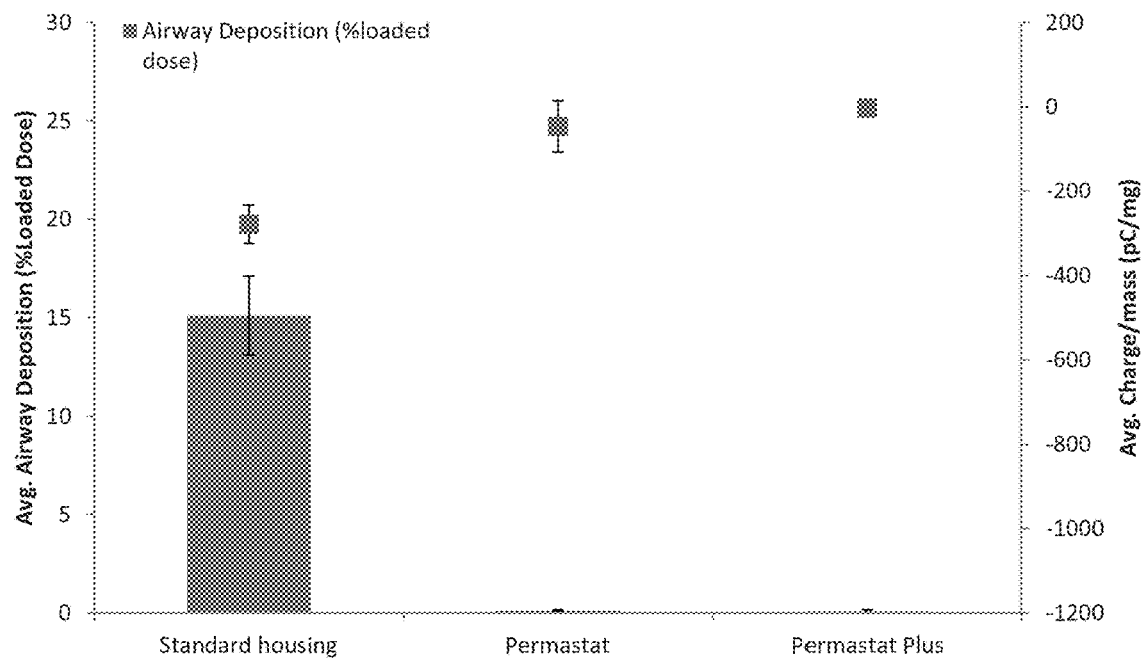
FIG. 2 is a graph showing airway deposition and aerosol charges for Permastat, Permastat Plus, and standard airway material.

Results: refer to Table 3 and FIG. 2.

Conclusion: Significant reduction in aerosol charging and airway deposition with Permastat and Permastat plus airways.

Example 39

II. Alprazolam airway deposition using anti-static spray and copper tape with ESD simulator or low humidity (#18 & 19)

Purpose:
To determine ways to reduce airway deposition
Materials/Equipment
General purpose staticide coated airway: sprayed inside and outside of airways with general purpose staticide
Heavy duty staticide coated airway: sprayed inside and outside of airways with heavy duty staticide
Electrical/copper airway: copper taped inside and outside of airways
Normal airway or control: Makrolon
ESD simulator
Drug: alprazolam
Experimental Setup
A. Airway deposition at ambient humidity (~41% RH-54% RH)
  Applied+16 kV onto airway using ESD simulator, charge on the drug side airway
  Generated aerosol at 15 LPM for devices with various airways: general purpose staticide coated airway, heavy duty staticide coated airway, and electrical/copper airway.
  Extracted airways with solvent and determined the drug amount deposited on the airways
B. Airway deposition at low humidity (~27% RH)
  Generated aerosol at 15 LPM for devices with various airways: general purpose staticide coated airway, electrical/copper airway, and normal airway
  Extracted airways with solvent and determined the drug amount deposited on the airways Results
A. Airway deposition at ambient humidity (~41% RH-54% RH)
B. Airway deposition at low humidity (~27% RH)

TABLE 4

| | A. ESD simulator (+16 kV) - ambient humidity | | | B. Low Humidity | | |
|---|---|---|---|---|---|---|
| | General purpose staticide (41% RH) | Heavy duty staticide (41% RH) | Electrical/ Copper tape (54% RH) | General purpose staticide (41% RH) | Heavy duty staticide (41% RH) | Control (Normal housing) |
| % Alprazolam on airway | 0.7 | 0.9 | 0.2 | 2.3 | 0.1 | 6.6 |
| | 0.3 | 0.6 | 0.1 | 0.4 | 0.1 | 13.1 |
| | 0.6 | 0.9 | 0.1 | 0.4 | 0.4 | 3.6 |

Both staticide and copper tape can substantially reduce airway deposition in either ambient or low humidity condition.

Example 40

III. Airway Deposition and Aerosol Charges of Various Airway (#35)
Purpose
To compare aerosol charge and airway deposition of various airways: normal airway, Metallizedairway (SS*/Cu/Cu/SS), and Permastat Plus airway.
Materials/Equipment
Standard airway material: Makrolon polycarbonate
Metallized airway: stainless steel/Copper/Copper/Stainless steel layers coated inside of the housing
Permastat Plus: surface resistivity ~1E9 ohm/sq
Experimental Setup:
Single dose Staccato device was placed in a mouthpiece that was attached to the aerosol electrometer
For studies where 16 kV+ was applied, an electrostatic gun (ESD simulator) was used to charge the airway
Aerosol generated at 28.3 LPM was captured in the aerosol electrometer and was measured in terms of current (pA)
The current measured was recorded by Tektronix scope and transferred to the computer Charge was calculated by integrating the current-time graph
Airway and HP were extracted for quant analysis (check for deposition)

zine, and zaleplon were used on the Staccato single dose platform. An electrostatic gun (ESD simulator) was used to charge the airway to amplify the effect of electrostatic effects.

TABLE 5

| Test # | airway | ESD gun | Aerosol Charge (pC) | Ave Aerosol Charge (pC) | Airway dep (%) | Ave Airway dep (%) | Airway dep (%) | HP dep (mg) | Emitted dose (mg) |
|---|---|---|---|---|---|---|---|---|---|
| 8 | Normal | no | -185.77 | -220.645 | 1 | 5 | 0.007 | 0.037 | 0.956 |
| 10 | | | -255.52 | | 9 | | 0.095 | 0.031 | 0.874 |
| 12 | | 16 kV+ | -199.01 | -220.405 | 2 | 8.5 | 0.024 | 0.033 | 0.943 |
| 14 | | | -241.8 | | 15 | | 0.15 | 0.035 | 0.815 |
| 9 | Metallized | no | -149.75 | -181.57 | 0 | 0 | 0 | 0.036 | 0.964 |
| 11 | | | -213.39 | | 0 | | 0.001 | 0.038 | 0.961 |
| 13 | | 16 kV+ | -303.15 | -111.63 | 0 | 0 | 0.001 | 0.028 | 0.971 |
| 15 | | | -18.74 | | 0 | | 0 | 0.041 | 0.959 |
| 20 | | | -13 | | 0 | | 0.002 | 0.035 | 0.963 |
| 18 | Permastat | no | -15.65 | -16.57 | 0 | 0 | 0 | 0.038 | 0.962 |
| 19 | Plus | | -17.49 | | 0 | | 0 | 0.037 | 0.963 |
| 16 | | 16 kV+ | -20.19 | -21.895 | 0 | 0 | 0.001 | 0.043 | 0.956 |
| 17 | | | -23.6 | | 0 | | 0 | 0.041 | 0.959 |

Metallized airway did not reduce aerosol charge but lowered airway deposition while Permastat Plus airway reduced both aerosol charge and airway deposition.

Example 41

IV. Aerosol properties using Permastat airway (#36)
Purpose
To evaluate aerosol properties using Permastat airway
Materials/Equipment
Staccato Alprazolam device built with Permastat housing
Staccato Alprazolam device built with normal Makrolon housing
Experimental Setup
Flow rate=28.3 LPM
Emitted dose, particle size, and emitted purity were collected for Permastat housing and normal Makrolon housing

TABLE 6

| | Normal Makrolon Material | | Permastat Material | |
|---|---|---|---|---|
| Attribute | Average | SD | Average | SD |
| Emitted Dose (% Loaded dose) | 109.5 | 3.8 | 94.7 | 3.1 |
| Heat Package Residual (% Loaded dose) | 5.1 | 0.7 | 4.8 | 0.5 |
| Airway Deposition (% Loaded dose) | 0.1 | 0.1 | 9.9 | 4.8 |
| MMAD (micron) | Did not conduct | | 1.2 | 0 |
| Purity (%) | 98.12 | 0.22 | 97.8 | 0.36 |

Figure 3:
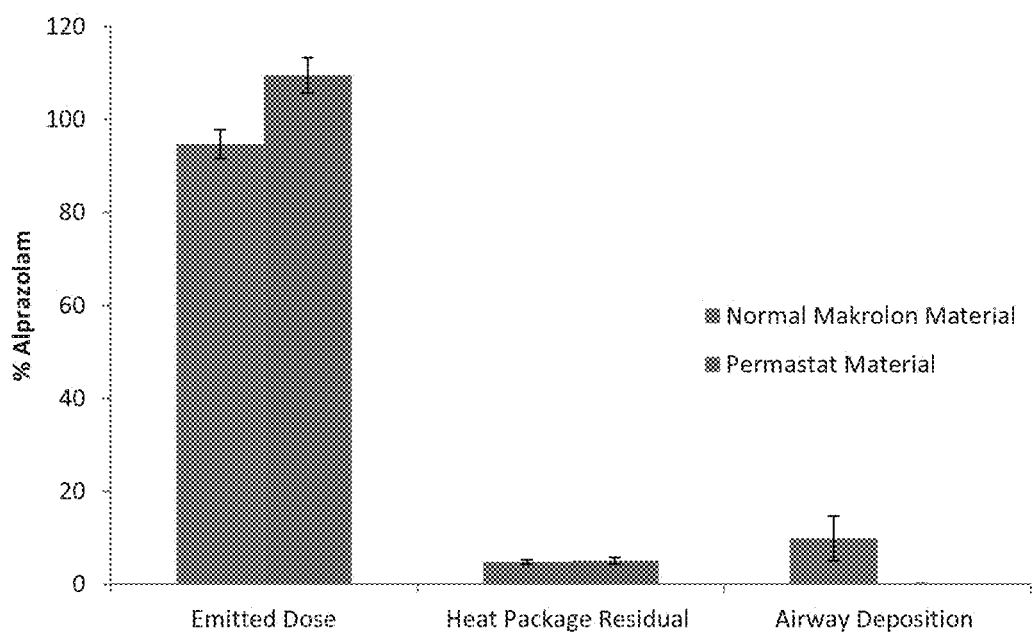
FIG. 3 is a graph showing the aerosol properties using Permastat airway.

See FIG. 3.

Emitted dose, particle size, and emitted purity using Permastat airway were good and within expectation. Almost zero deposition was found on the Permastat airway.

Example 42

I. Net Charge and Aerosol Deposition on Airway for Various Drugs (Pulling from Multiple Studies)
Several benzodiazepine drugs (alprazolam, estazolam, triazolam, diazepam, clobazam), loxapine, prochlorpera-

TABLE 7

| Drug | Applied Potential to Airway Housing | 1a. Net Charge Net charge (pC/mg) | 1b. Housing Deposition Aerosol deposition on housing (% Loaded Dose) |
|---|---|---|---|
| Alprazolam | +16 kV | N/A | 45 ± 6 |
| | -16 kV | | 12 ± 4 |
| | None | -252 ± 59 | 12 ± 6 |
| Estazolam | None | -202 ± 3 | N/A |
| Triazolam | None | -158 ± 13 | |
| Diazepam | None | -1 ± 1 | |
| Clobazam | None | 0 ± 0 | |
| Prochlorperazine | +16 kV | N/A | 7 |
| | -16 kV | | 3 |
| | None | 27 ± 3 | 3 ± 3 |
| Loxapine | +16 kV | N/A | 0 |
| | -16 kV | | 1 |
| | None | | 2 ± 2 |
| Zaleplon | +16 kV | -15 ± 6 | N/A |
| | -16 kV | 2 ± 8 | |
| | None | 7 ± 1 | 0 ± 0 |

One of ordinary skill in the art would understand that the experimental device detailed above could be transformed into an inhalation delivery device by excluding the sealed vial and including a housing to contain the assembly and electrical components. The housing would contain an air inlet and a mouthpiece such that, when drug volatilization occurred, an inhaled breath would carry the formed aerosol into the lungs of a subject.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. Many other variations are also to be considered within the scope of the present invention.

What is claimed is:

1. A device for delivering a thermal condensation aerosol comprising:

a solid support, a thin layer of a drug composition coated on the solid support, wherein the drug composition alprazolam, a housing defining an airway, wherein the airway housing comprises an antistatic material, wherein the housing cools a drug vapor which is generated by heating the alprazolam to form the condensation aerosol, wherein the heating is via breath actuation, wherein a heat source supplies heat to the solid support at a rate that achieves a support temperature of at least 300° C. and produces substantially complete vaporization of the alprazolam from the solid support within a period of 2 seconds, and wherein said condensation aerosol is completely devoid of organic solvents, propellants, and any excipients.

2. The device of claim 1, wherein the antistatic material is coated on an inner wall of the airway housing.

3. The device of claim 2, wherein the antistatic material is comprised of metallized airways, wherein the metallized airways are produced by coating the inner wall of the airway housing with conductive metals.

4. The device of claim 3, wherein the conductive metals comprise a stacking of stainless steel, copper, copper, and stainless steel in four separate layers.

5. The device of claim 1, wherein the antistatic material is comprised of a metallic tape applied to the inner wall and an outer wall of the airway housing.

6. The device of claim 1, wherein the antistatic material is comprised of an antistatic spray applied on a default airway housing.

7. The device of claim 1, wherein the antistatic material is comprised of antistatic plastics applied as airway housing materials.

8. The device of claim 7, wherein the antistatic plastics is anti-static polycarbonate.

9. A method for producing drug condensation aerosol to administer to a patient by inhalation in a drug delivery device, wherein the condensation aerosol is formed by heating a thin layer containing alprazolam, on a solid support, to produce a vapor of the alprazolam, wherein the heating is via breath actuation, and wherein a heat source supplies heat to the solid support at a rate that achieves a support temperature of at least 300° C. and produces substantially complete vaporization of the alprazolam from the solid support within a period of 2 seconds, and condensing the vapor to form a condensation aerosol characterized by less than 10% drug degradation products by weight, and an MMAD of less than 5 microns, and wherein said condensation aerosol is completely devoid of organic solvents, propellants, and any excipients;

wherein an airway housing in the drug delivery device comprises an antistatic material and wherein the vapor is condensed through cooling in an airway.

10. The method of claim 9, wherein the antistatic material is coated on an inner wall of the airway housing.

11. The method of claim 9, wherein the antistatic material is comprised of metallized airways, wherein an inner wall of the airway housing is coated with conductive metals.

12. The method of claim 11, wherein the conductive metals comprise a stacking of stainless steel, copper, copper, and stainless steel in four separate layers.

13. The method of claim 9, wherein the antistatic material is comprised of a metallic tape applied to an inner wall and an outer wall of the airway housing.

14. The method of claim 9, wherein the antistatic material is comprised of an antistatic spray applied on a default airway housing.

15. The method of claim 9, wherein the antistatic material is comprised of antistatic plastics applied as airway housing materials.

16. The method of claim 15, wherein the antistatic plastics is anti-static polycarbonate.

* * * * *

UNITED STATES PATENT AND TRADEMARK OFFICE
CERTIFICATE OF CORRECTION

PATENT NO. : 11,511,054 B2
APPLICATION NO. : 15/557030
DATED : November 29, 2022
INVENTOR(S) : Daniel J. Myers, Khe Kubel and James Cassella It is certified that error appears in the above-identified patent and that said Letters Patent is hereby corrected as shown below:

In the Claims

At Column 37, Lines 5-6:
"wherein the drug composition alprazolam" should read --wherein the drug composition comprises alprazolam--

Signed and Sealed this
Eleventh Day of June, 2024

*Katherine Kelly Vidal*

Katherine Kelly Vidal
*Director of the United States Patent and Trademark Office*